(12) United States Patent
Taki et al.

(10) Patent No.: US 10,643,636 B2
(45) Date of Patent: May 5, 2020

(54) INFORMATION PROCESSING APPARATUS, INFORMATION PROCESSING METHOD, AND PROGRAM

(71) Applicant: SONY CORPORATION, Tokyo (JP)

(72) Inventors: Yuhei Taki, Kanagawa (JP); Yoko Ito, Tokyo (JP); Shinichi Kawano, Tokyo (JP)

(73) Assignee: SONY CORPORATION, Tokyo (JP)

( * ) Notice: Subject to any disclaimer, the term of this patent is extended or adjusted under 35 U.S.C. 154(b) by 63 days.

(21) Appl. No.: 15/736,509

(22) PCT Filed: May 23, 2016

(86) PCT No.: PCT/JP2016/065192
§ 371 (c)(1),
(2) Date: Dec. 14, 2017

(87) PCT Pub. No.: WO2017/029850
PCT Pub. Date: Feb. 23, 2017

(65) Prior Publication Data
US 2018/0197564 A1    Jul. 12, 2018

(30) Foreign Application Priority Data

Aug. 20, 2015    (JP) .................................. 2015-162620

(51) Int. Cl.
*G10L 15/00*    (2013.01)
*G10L 21/10*    (2013.01)
(Continued)

(52) U.S. Cl.
CPC .............. *G10L 21/10* (2013.01); *A61B 5/123* (2013.01); *A61B 5/6898* (2013.01); *A61B 5/741* (2013.01); *G06F 3/167* (2013.01); *G10L 15/22* (2013.01); *G10L 15/265* (2013.01); *A61B 5/0022* (2013.01); *A61B 5/744* (2013.01); *A61B 5/7435* (2013.01); *A61B 5/7465* (2013.01); *A61B 5/7475* (2013.01); *A61B 2505/07* (2013.01); *G10L 2021/065* (2013.01)

(58) Field of Classification Search
CPC ........ G10L 13/033; G10L 13/08; G10L 15/00
See application file for complete search history.

(56) References Cited

U.S. PATENT DOCUMENTS

2007/0208566 A1* 9/2007 En-Najjary ........... G10L 13/033
704/269
2010/0324894 A1* 12/2010 Potkonjak ............. G06F 17/289
704/235

(Continued)

*Primary Examiner* — Daniel Abebe
(74) *Attorney, Agent, or Firm* — Paratus Law Group, PLLC

(57) ABSTRACT

There is provided an information processing apparatus capable of enhancing the possibility of outputting information with granularity desired by a user, the information processing apparatus including: a generation unit configured to generate second text data on a basis of first text data and information regarding a first user's auditory characteristics; and an output unit configured to output output information regarding the second text data. The generation unit controls granularity of the second text data on a basis of the information regarding the first user's auditory characteristics.

20 Claims, 24 Drawing Sheets

(51) Int. Cl.
*A61B 5/00* (2006.01)
*A61B 5/12* (2006.01)
*G10L 15/22* (2006.01)
*G06F 3/16* (2006.01)
*G10L 15/26* (2006.01)
*G10L 21/06* (2013.01)

(56) References Cited

U.S. PATENT DOCUMENTS

| | | | |
|---|---|---|---|
| 2014/0019135 A1* | 1/2014 | Talwar | F10L 13/08 |
| | | | 704/260 |
| 2016/0352895 A1* | 12/2016 | Son | G10L 13/033 |
| 2017/0221470 A1* | 8/2017 | Kayama | G10L 25/90 |
| 2017/0243582 A1* | 8/2017 | Menezes | G10L 13/0335 |
| 2018/0247637 A1* | 8/2018 | Lacoss-Arnold | G06F 3/0481 |

* cited by examiner

FIG. 1
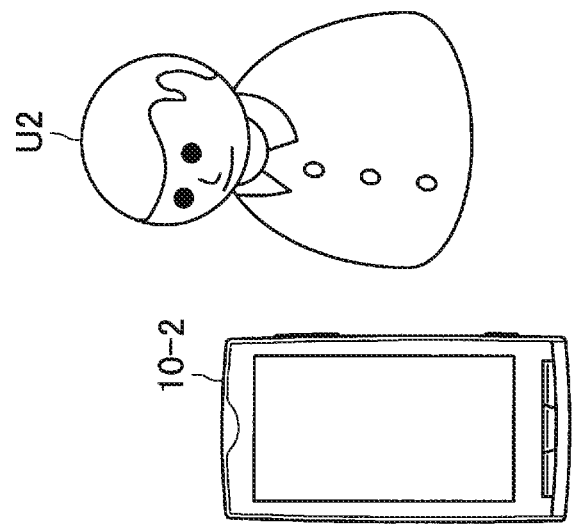
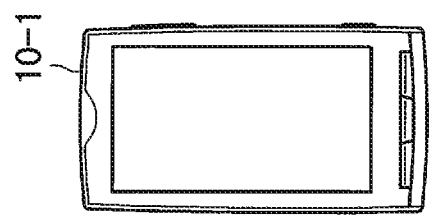
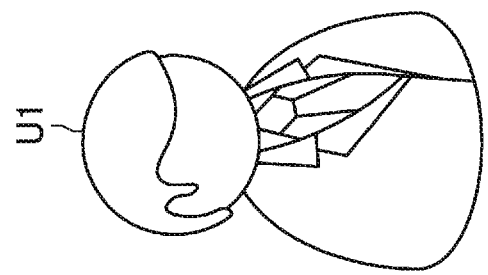

FIG. 5

| FORMANT | i | e | a | o | u |
|---|---|---|---|---|---|
| FIRST | 338.4 | 502.2 | 718.2 | 496.5 | 326.1 |
| SECOND | 2127.9 | 1965.3 | 1145.9 | 859.1 | 1435.1 |

FIG. 6

| VOICE RECOGNITION RESULT | At 10:00am of Saturday. | | | |
|---|---|---|---|---|
| AFTER PHRASAL ANALYSIS | At | 10:00am | of | Saturday. |
| NUMBER OF VOWEL ELEMENTS V_txt REQUIRING CONVERSION-TO-TEXT | 0 | 4 | 0 | 2 |
| CASE WHERE THRESHOLD V_txt_th OF NUMBER OF VOWEL ELEMENTS REQUIRING CONVERSION-TO-TEXT = 1 | NOT CONVERTED TO TEXT | CONVERTED TO TEXT | NOT CONVERTED TO TEXT | CONVERTED TO TEXT |

FIG. 12

| LANGUAGE | BASS BAND |
|---|---|
| JAPANESE | 125 HERTZ ~ 1500 HERTZ |
| ENGLISH | 2000 HERTZ ~ 12000 HERTZ |
| ITALIAN | 2000 HERTZ ~ 4000 HERTZ |
| GERMAN | 125 HERTZ ~ 3000 HERTZ |
| RUSSIAN | 125 HERTZ ~ 8000 HERTZ |

FIG. 13

JAPANESE (UNIT : kHz)

| FORMANT | A | I | U | E | O |
|---|---|---|---|---|---|
| FIRST FORMANT | 1.0 | 0.4 | 0.5 | 0.7 | 0.7 |
| SECOND FORMANT | 1.2 | 2.8 | 1.2 | 2.0 | 1.0 |

FIG. 14

ENGLISH (UNIT : kHz)

| FORMANT | A | I | U | E | O |
|---|---|---|---|---|---|
| FIRST FORMANT | 0.8 | 0.3 | 0.3 | 0.9 | 0.6 |
| SECOND FORMANT | 1.5 | 2.5 | 0.8 | 2.0 | 0.8 |

FIG. 24
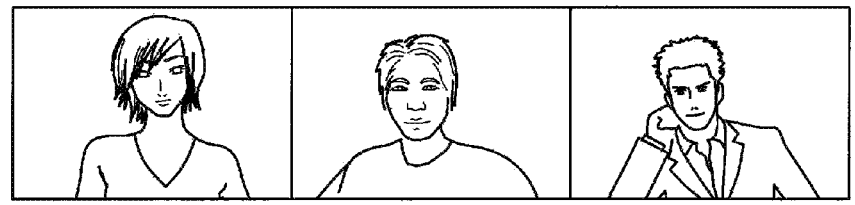
- Saturday
- 10:00am
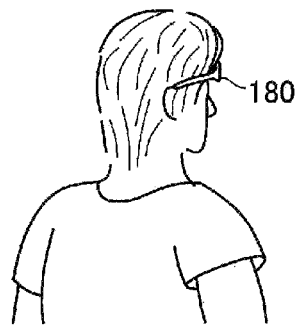
FIG. 25
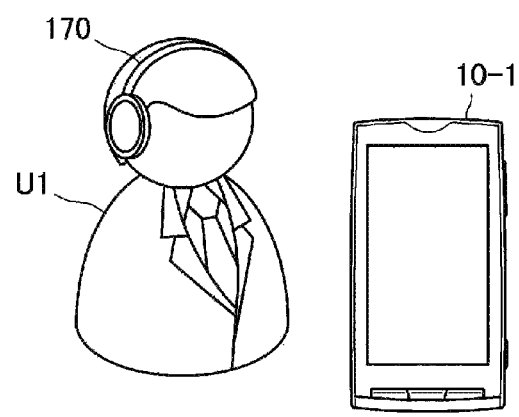

INFORMATION PROCESSING APPARATUS, INFORMATION PROCESSING METHOD, AND PROGRAM

CROSS REFERENCE TO PRIOR APPLICATION

This application is a National Stage Patent Application of PCT International Patent Application No. PCT/JP2016/065192 (filed on May 23, 2016) under 35 U.S.C. § 371, which claims priority to Japanese Patent Application No. 2015-162620 (filed on Aug. 20, 2015), which are all hereby incorporated by reference in their entirety.

TECHNICAL FIELD

The present disclosure relates to an information processing apparatus, an information processing method, and a program.

BACKGROUND ART

In recent years, various technologies have been disclosed as technologies for supporting perception of sound information by a user. For example, a technology is disclosed in which a user who attempts to perceive sound information using a hearing aid is caused to view display corresponding to a result of voice recognition performed on the sound information (e.g., see Patent Literature 1).

CITATION LIST

Patent Literature

Patent Literature 1: JP 2001-25096A

DISCLOSURE OF INVENTION

Technical Problem

However, a success rate of a user catching sound information may change in accordance with the user's auditory characteristics. Therefore, granularity of information desired by the user may also change in accordance with the user's auditory characteristics. Hence, it is desirable to provide a technology capable of enhancing the possibility of outputting information with granularity desired by a user.

Solution to Problem

According to the present disclosure, there is provided an information processing apparatus including: a generation unit configured to generate second text data on a basis of first text data and information regarding a first user's auditory characteristics; and an output unit configured to output output information regarding the second text data. The generation unit controls granularity of the second text data on a basis of the information regarding the first user's auditory characteristics.

According to the present disclosure, there is provided an information processing method including: generating second text data on a basis of first text data and information regarding a first user's auditory characteristics; outputting output information regarding the second text data; and controlling, by a processor, granularity of the second text data on a basis of the information regarding the first user's auditory characteristics.

According to the present disclosure, there is provided a program for causing a computer to function as an information processing apparatus including: a generation unit configured to generate second text data on a basis of first text data and information regarding a first user's auditory characteristics; and an output unit configured to output output information regarding the second text data. The generation unit controls granularity of the second text data on a basis of the information regarding the first user's auditory characteristics.

Advantageous Effects of Invention

As described above, according to the present disclosure, a technology capable of enhancing the possibility of outputting information with granularity desired by a user is provided. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 illustrates a configuration example of an information processing system according to an embodiment of the present disclosure.

FIG. 5 shows examples of a frequency corresponding to a vowel element.

FIG. 6 is a diagram for describing an example of processing executed after a voice recognition result is obtained until output information corresponding to the voice recognition result is output.

FIG. 12 shows an example of a frequency band (passband) of voice spoken in each language.

FIG. 13 shows examples of the first formant and the second formant in Japanese.

FIG. 14 shows examples of the first formant and the second formant in English.

FIG. 24 illustrates a case where an information processing apparatus is a HMD.

FIG. 25 is a diagram for describing a case where output information includes sound information generated on the basis of output text data.

MODE(S) FOR CARRYING OUT THE INVENTION

Figure 2:
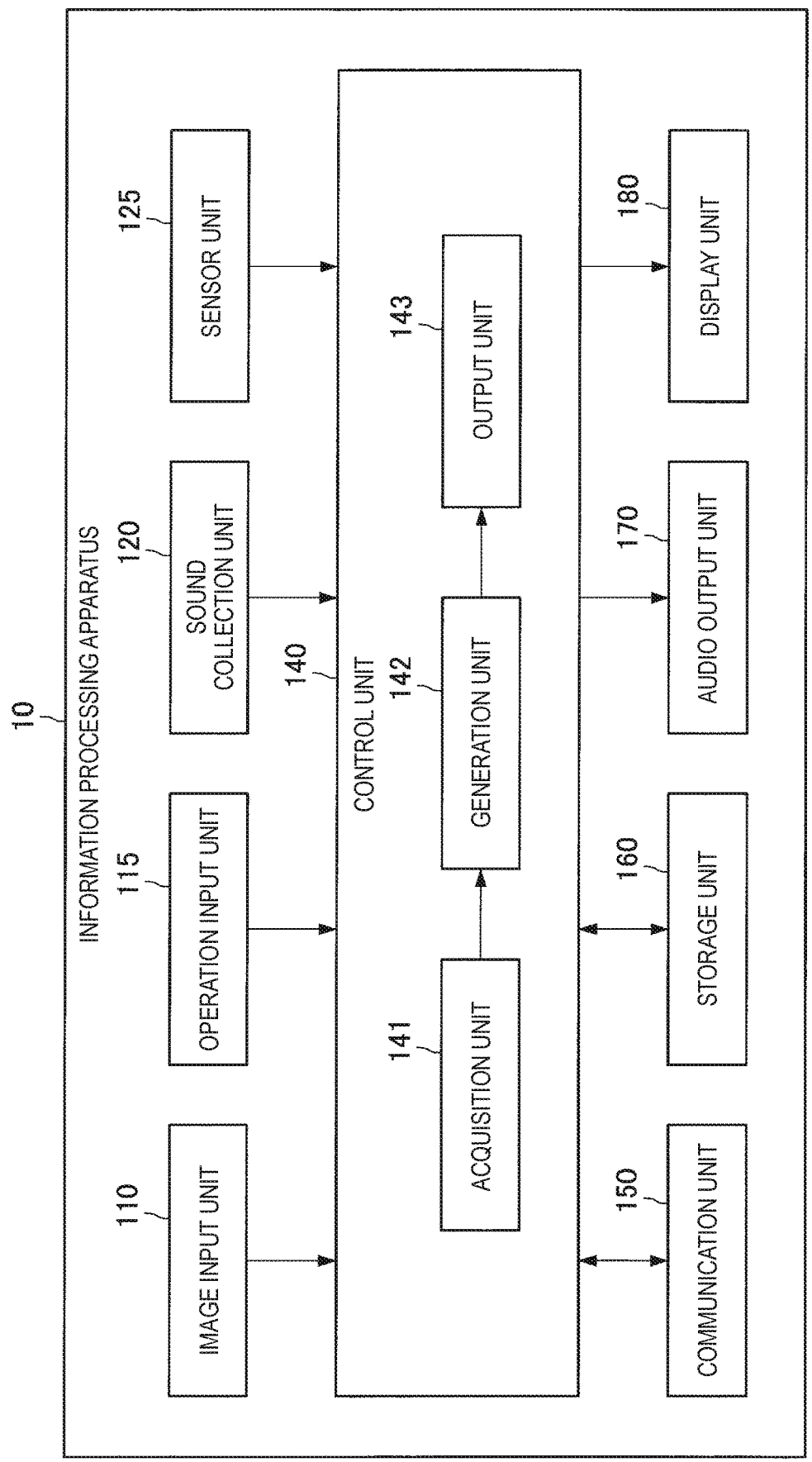
FIG. 2 is a block diagram illustrating a functional configuration example of an information processing apparatus according to the embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that, in this description and the drawings, structural elements that have substantially the same function and structure are sometimes distinguished from each other using different numbers after the same reference sign. However, when there is no need in particular to distinguish structural elements that have substantially the same function and structure, the same reference sign alone is attached.

Description will be given in the following order.
1. Embodiment of present disclosure
   1.1. System configuration example
   1.2. Functional configuration example
   1.3. Functional details of information processing system
   1.4. Operation example of information processing apparatus
   1.5. Various modification examples
   1.6. Hardware configuration example
2. Conclusion

1. EMBODIMENT OF PRESENT DISCLOSURE 1.1. System Configuration Example

First, description will be given on a configuration example of an information processing system 1 according to an embodiment of the present disclosure, with reference to a drawing. FIG. 1 illustrates a configuration example of the information processing system 1 according to an embodiment of the present disclosure. As illustrated in FIG. 1, the information processing system 1 according to an embodiment of the present disclosure includes an information processing apparatus 10-1 and an information processing apparatus 10-2. The information processing apparatus 10-1 is used by a user U1, and the information processing apparatus 10-2 is used by a user U2.

For example, the information processing apparatus 10-1 and the information processing apparatus 10-2 each have a telephone function. This telephone function enables the user U1 and the user U2 to transmit sound information including one's own spoken voice to the partner via the information processing apparatus 10-1 and the information processing apparatus 10-2 while the information processing apparatus 10-1 and the information processing apparatus 10-2 are in telephone connection. Described below is an example in which the information processing apparatus 10-1 and the information processing apparatus 10-2 each have a telephone function, but the information processing apparatus 10-1 and the information processing apparatus 10-2 each need not have a telephone function, as will be described later.

Note that FIG. 1 illustrates an example in which the information processing apparatus 10-1 and the information processing apparatus 10-2 are each a smartphone, but the information processing apparatus 10-1 and the information processing apparatus 10-2 are not particularly limited in form. For example, the information processing apparatus 10-1 and the information processing apparatus 10-2 each may be a mobile phone, a game console, or the like. In addition, in the following description, "voice" or "speech" is distinguished from "sound".

The configuration of the information processing system 1 has been described.

1.2. Functional Configuration Example

Now, a functional configuration example of the information processing apparatus 10 will be described. FIG. 2 is a block diagram illustrating a functional configuration example of the information processing apparatus 10. As illustrated in FIG. 2, the information processing apparatus 10 includes an image input unit 110, an operation input unit 115, a sound collection unit 120, an output unit 130, a sensor unit 125, a control unit 140, a communication unit 150, a storage unit 160, an audio output unit 170, and a display unit 180.

The image input unit 110 has a function of inputting an image. The image input unit 110 includes a camera, and inputs an image captured by the camera. The number of the cameras included in the image input unit 110 is not particularly limited as long as it is one or more. In addition, positions where the one or more cameras included in the image input unit 110 are provided are also not particularly limited. Moreover, the one or more cameras may include a monocular camera or a stereo camera.

The operation input unit 115 has a function of inputting operation by a user U. For example, the operation input unit 115 may include a touch panel. The type of the touch panel is not particularly limited, and may be a capacitive type, a resistive type, an infrared type, or a SAW type. In addition, the operation input unit 115 need not be a touch panel as long as it has a function of inputting operation by the user U, and may be, for example, a camera or a hardware button.

The sound collection unit 120 has a function of obtaining sound information by sound collection. For example, the sound collection unit 120 may include a microphone that is present at an upper end of a smartphone. Note that the number of the microphones included in the sound collection unit 120 is not particularly limited as long as it is one or more. In addition, positions where the one or more microphones included in the sound collection unit 120 are provided are also not particularly limited.

However, if the sound collection unit 120 includes a plurality of microphones, it is possible to estimate a direction from which sound comes on the basis of sound information obtained by sound collection by each of the plurality of microphones. In addition, if the sound collection unit 120 includes a microphone having directivity, it is possible to estimate a direction from which sound comes on the basis of sound information obtained by sound collection by the microphone having directivity.

The sensor unit 125 has a function of detecting sensor data on which activity information of a user and biological information of a user are based. For example, if the sensor unit 125 includes an acceleration sensor and an angular velocity sensor, a generation unit 142 can estimate activity information on the basis of an acceleration detected by the acceleration sensor, an angular velocity detected by the angular velocity sensor, etc. In addition, if the sensor unit 125 includes a sensor capable of detecting sensor data related to a body, the generation unit 142 can estimate biological information on the basis of sensor data related to a body.

The control unit 140 controls each unit of the information processing apparatus 10. As illustrated in FIG. 2, the control unit 140 includes an acquisition unit 141, the generation unit 142, and an output unit 143. Details about these functional blocks will be described later. Note that the control unit 140 may include, for example, a central processing unit (CPU) or the like. In the case where the information processing apparatus 140 includes a processing device such as a CPU, the processing device may include an electronic circuit.

The communication unit 150 has a function of communicating with another information processing apparatus 10. For example, the communication unit 150 includes a communication interface. For example, the communication unit 150 can communicate with another information processing apparatus 10 by a telephone function. The storage unit 160 has a function of storing various data needed for operation performed by the control unit 140. For example, the storage unit 160 includes a storage device. The audio output unit 170 has a function of outputting sound information. For example, the audio output unit 170 may be a speaker or a headphone.

The display unit 180 has a function of displaying a screen. The output unit 180 is stacked on the operation input unit 115, and corresponding positions of the operation input unit 115 and the output unit 180 overlap each other. Note that a position where the output unit 180 is provided is not particularly limited. In addition, the display unit 180 typically may be a liquid crystal display, an organic electroluminescence (EL) display, a head mount display (HMD), or the like, but may be a display in another form as long as it has a function of displaying a screen.

The functional configuration example of the information processing apparatus 1 has been described.

1.3. Functional Details of Information Processing System

Now, functional details of the information processing system 1 will be described. First, the following scene is assumed: using the information processing apparatus 10-1, the user U1 has a phone conversation by a telephone function with the user U2 using the information processing apparatus 10-2. Here, it is presumed that a success rate of the user U1 catching sound information may change in accordance with the user U1's auditory characteristics. Therefore, granularity of information desired by the user U1 may also change in accordance with the user U1's auditory characteristics. Hence, it is desirable to provide a technology capable of enhancing the possibility of outputting information with granularity desired by the user U1.

Specifically, in the information processing apparatus 10-1, the generation unit 142 performs voice recognition processing on sound information including spoken voice of the user U2, who is the phone conversation partner, and generates second text data (hereinafter referred to as "output text data") on the basis of a voice recognition result (an example of first text data) obtained by the voice recognition processing and information regarding the user U1's auditory characteristics. Then, the output unit 143 outputs output information regarding the output text data. For example, the output information is displayed by the display unit 180 in the information processing apparatus 10-1, and is visually perceived by the user U1.

At this time, the generation unit 142 controls granularity of the output text data on the basis of the information regarding the user U1's auditory characteristics. This control can enhance the possibility of outputting information with granularity desired by the user U1.

These functional details are further specifically described below. First, the acquisition unit 141 acquires information regarding the user U1's auditory characteristics. There is no particular limitation on a technique for the acquisition unit 141 to acquire the information regarding the user U1's auditory characteristics. As an example, the acquisition unit 141 may acquire the information regarding the user U1's auditory characteristics on the basis of a result of a test related to the user U1's auditory sense, which is performed in advance.

Figure 3:
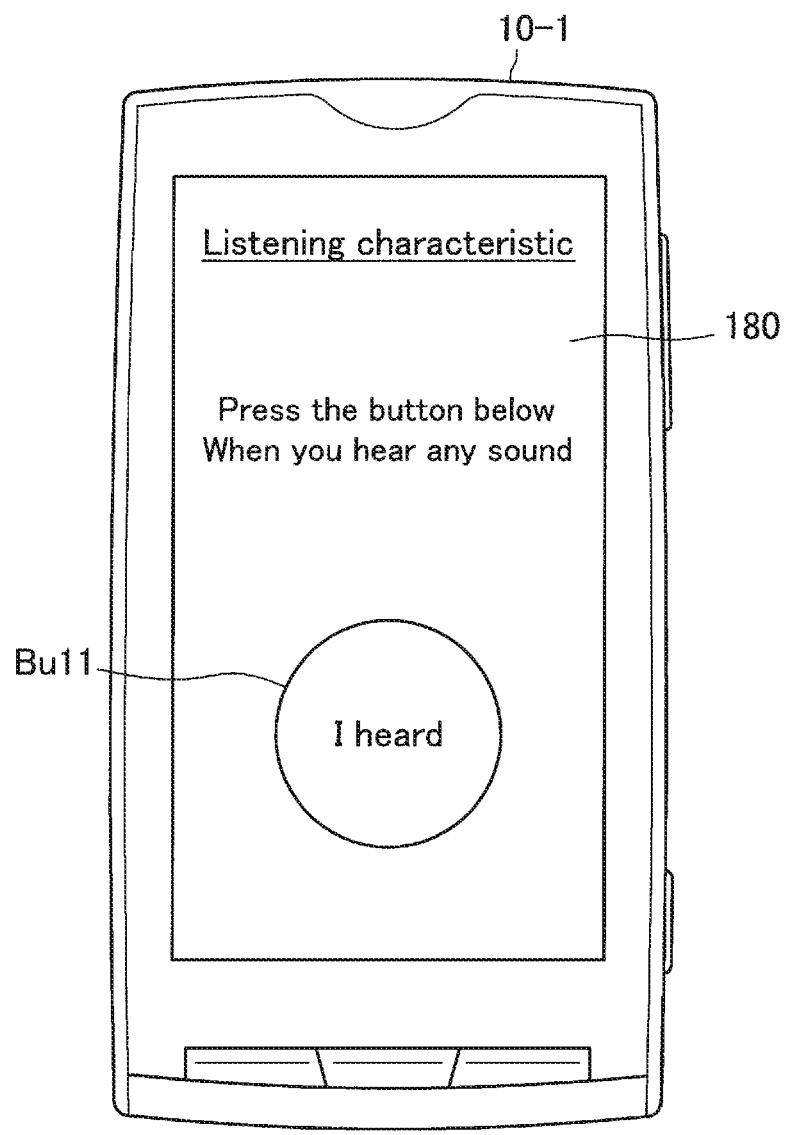
FIG. 3 illustrates an example of a screen that is used for a test related to auditory sense.

FIG. 3 illustrates an example of a screen that is used for a test related to auditory sense. According to FIG. 3, in the information processing apparatus 10-1 of the user U1, the display unit 180 displays a button Bu11. In addition, according to FIG. 3, the display unit 180 displays guidance that encourages the user U1 to press the button Bu11 when hearing a sound produced for the test. The acquisition unit 141 can acquire, as a hearing level, volume that the user U1 can catch for each frequency, by inspecting whether the user U1 normally presses the button Bu11 in response to production of a sound while changing frequency and volume.

The hearing level for each frequency of the user U1 obtained in this manner is acquired as information regarding the user U1's auditory characteristics by the acquisition unit 141. Subsequently, the generation unit 142 preferably extracts, as one or more pieces of extracted data, one or more pieces of text data satisfying a predetermined relationship with a predetermined frequency region in which the user's hearing level is low, from the voice recognition result, and generates output text data to so as include the one or more pieces of extracted data. This configuration can further enhance the possibility of outputting information with granularity desired by the user U1.

Figure 4:
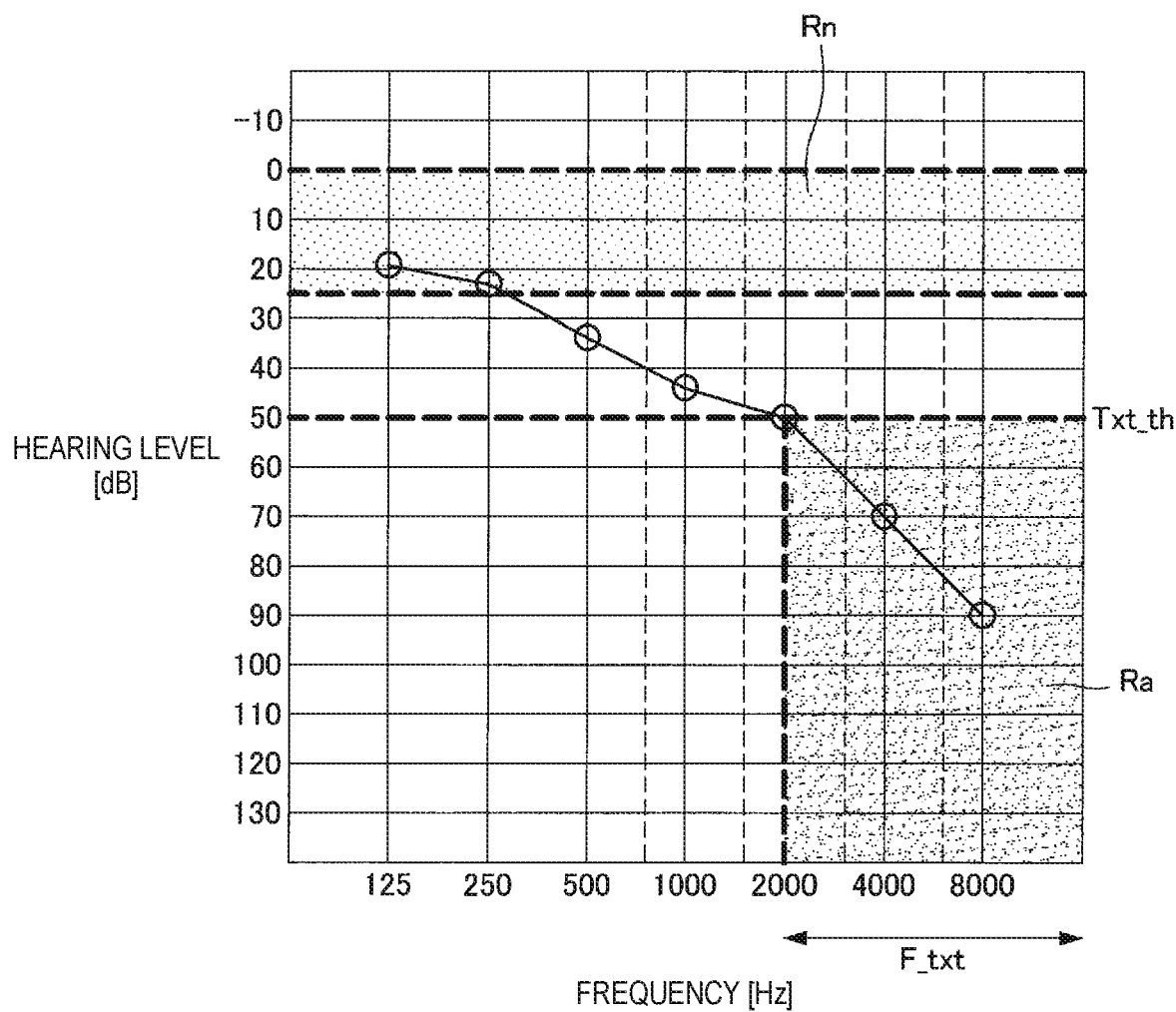
FIG. 4 illustrates an example of information regarding a user's auditory characteristics.

The predetermined frequency region may include a range of frequencies in which the user U1's hearing level is lower than a predetermined hearing level threshold. The predetermined hearing level threshold is acquired by the acquisition unit 141. Hereinafter, the predetermined frequency region will be referred to as a "frequency region F_txt requiring conversion-to-text" and the predetermined hearing level threshold will be referred to as a "threshold Txt_th of a level requiring conversion-to-text" in some cases. FIG. 4 illustrates an example of information regarding the user U1's auditory characteristics. As illustrated in FIG. 4, the information regarding the user U1's auditory characteristics indicates the user U1's hearing level at each frequency.

In addition, FIG. 4 shows the threshold Txt_th of the level requiring conversion-to-text. FIG. 4 also shows, as the frequency region F_txt requiring conversion-to-text, a range of frequencies in which the user U1's hearing level is lower than the threshold Txt_th of the level requiring conversion-to-text (i.e., a volume level that the user U1 can catch is greater than the threshold Txt_th of the level requiring conversion-to-text). Furthermore, a range that is normally catchable in general is shown as "Rn", and a range that is difficult for the user U1 to catch is shown as "Ra".

Here, in human auditory sense, greater difficulty in catching a vowel usually results in greater difficulty in identifying sound including the vowel as an element. In addition, a vowel includes one or more frequency components. Hence, the generation unit 142 preferably divides the voice recognition result into a plurality of pieces of divided data, and calculates, for each of one or more pieces of divided data, the number of vowel elements (hereinafter also referred to as "vowel elements V_txt requiring conversion-to-text") of which at least one of corresponding one or more frequencies belongs to the frequency region F_txt requiring conversion-to-text.

Then, the generation unit 142 preferably extracts, as one or more pieces of extracted data, one or more pieces of divided data for which the calculated number exceeds a predetermined number threshold (hereinafter also referred to as a "vowel element V_txt_th requiring conversion-to-text"), among the plurality of pieces of divided data. Generating output text data so as to include the one or more pieces of extracted data extracted in this manner can further enhance the possibility of outputting information with granularity desired by the user U1. Further description will be given on examples of a frequency corresponding to a vowel element. FIG. 5 shows examples of a frequency corresponding to a vowel element.

According to FIG. 5, two frequencies corresponding to each of five vowel elements (i, e, a, o, u) are shown. Here, the lower one of voices having the two frequencies corresponding to each vowel element is referred to as a "first formant", and the higher one is referred to as a "second formant". FIG. 5 shows frequencies of the "first formant" and the "second formant" corresponding to each of the five vowel elements (i, e, a, o, u). Hereinafter, description will be given using the "first formant" and the "second formant" as examples of one or more frequencies corresponding to a vowel element.

In addition, the generation unit 142 may divide a voice recognition result in any units. For example, the generation unit 142 may divide the voice recognition result in units of phrases by performing phrasal analysis on the voice recognition result. Described below is an example in which a voice recognition result is divided in units of phrases in this manner. Now, description will be given on an example of processing executed by the information processing apparatus 10-1 after "At 10:00 am of Saturday." is obtained, as an example of a voice recognition result, until output information corresponding to this voice recognition result is output.

FIG. 6 is a diagram for describing an example of processing executed after a voice recognition result is obtained until output information corresponding to the voice recognition result is output. As shown in FIG. 6, a case where the generation unit 142 obtains "At 10:00 am of Saturday." as an example of a voice recognition result is assumed. At this time, the generation unit 142 can perform phrasal analysis on "At 10:00 am of Saturday." to obtain "At", "10:00 am", "of", and "Saturday." as phrases as shown in FIG. 6.

Subsequently, the generation unit 142 can phonetically break down each of "At", "10:00 am", "of", and "Saturday." and obtain the numbers of vowel elements of which at least one of frequencies of the "first formant" and the "second formant" belongs to the frequency region F_txt requiring conversion-to-text, as the numbers "0", "4", "0", and "2" of the vowel elements V_txt requiring conversion-to-text. Phonetic breakdown is performed because a voice recognition result may include a letter that is not pronounced. Here, as an example, a case where the threshold V_txt_th of the number of vowel elements requiring conversion-to-text=1 is set is assumed.

At this time, as shown in FIG. 6, by the generation unit 142, "10:00 am" and "Saturday." corresponding to the numbers "4" and "2" of the vowel elements V_txt requiring conversion-to-text that exceed the threshold V_txt_th of the number of vowel elements requiring conversion-to-text=1, among the numbers "0", "4", "0", and "2" of the vowel elements V_txt requiring conversion-to-text of "At", "10:00 am", "of", and "Saturday.", are "converted to text". On the other hand, "At" and "of" corresponding to the numbers "0" and "0" of the vowel elements V_txt requiring conversion-to-text that do not exceed the threshold V_txt_th of the number of vowel elements requiring conversion-to-text=1 are "not converted to text".

Figure 7:
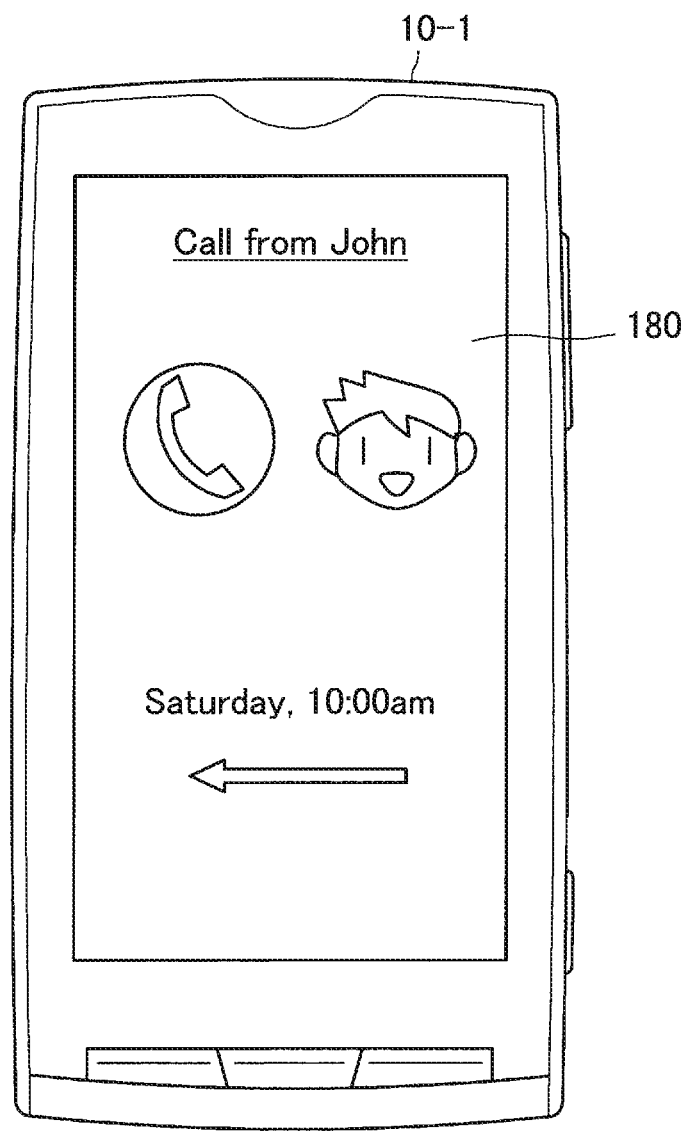
FIG. 7 illustrates a display example of output information.

The generation unit 142 can generate output text data including "10:00 am" and "Saturday." that are "converted to text" (excluding "At" and "of" that are "not converted to text"). The output unit 143 can output output information regarding the output text data generated in this manner. FIG. 7 illustrates a display example of output information. For example, when output information is displayed by the display unit 180 in the information processing apparatus 10-1, as illustrated in FIG. 7, the output information is visually perceived by the user U1. According to FIG. 7, it is understood that information "Saturday" and "10:00 am" with granularity desired by the user U1 is output.

The functional details of the information processing system 1 have been described. Here, the above description is given assuming that the threshold Txt_th of the level requiring conversion-to-text is constant, but the threshold Txt_th of the level requiring conversion-to-text may be updated. For example, it is assumed that difficulty in hearing sound information may change in accordance with an environment where the user U1 is present. Hence, the generation unit 142 may update the threshold Txt_th of the level requiring conversion-to-text on the basis of information regarding the environment where the user U1 is present.

Information regarding environment may be environmental noise. Environmental noise may be defined in various ways, and may be collected sound other than the spoken voice of U2, who is the phone conversation partner. Here, it is presumed that larger environmental noise leads to greater difficulty in the user U1 catching sound information. Therefore, the generation unit 142 may update the threshold Txt_th of the level requiring conversion-to-text in a manner that the threshold Txt_th of the level requiring conversion-to-text increases as noise in the environment where the user U1 is present becomes larger.

For example, it is assumed that difficulty in hearing sound information may change in accordance with activity information or biological information of the user U1. Hence, the generation unit 142 may update the threshold Txt_th of the level requiring conversion-to-text on the basis of the activity information or the biological information of the user U1.

For example, difficulty in hearing sound information may differ depending on whether the user U1 is sitting, standing still, walking, running, taking a train, or driving a car. Hence, the generation unit 142 may update the threshold Txt_th of the level requiring conversion-to-text to a new threshold Txt_th of a level requiring conversion-to-text that corresponds to the activity information of the user U1.

Alternatively, difficulty in hearing sound information may change depending on a heart rate of the user U1. Similarly, difficulty in hearing sound information may change depending on body temperature, a perspiration amount, a pulse rate, the number of times of breathing, the number of times of blinking, eye movement, gaze time, a pupil diameter, blood pressure, brain waves, body motion, posture, skin temperature, electric resistance of skin, micro-vibration (MV), myo-electric potential, and blood oxygen saturation ($SPO_2$) of the user U1. Hence, the generation unit 142 may update the threshold Txt_th of the level requiring conversion-to-text to a new threshold Txt_th of a level requiring conversion-to-text that corresponds to such biological information.

1.4. Operation Example of Information Processing Apparatus

Figure 8:
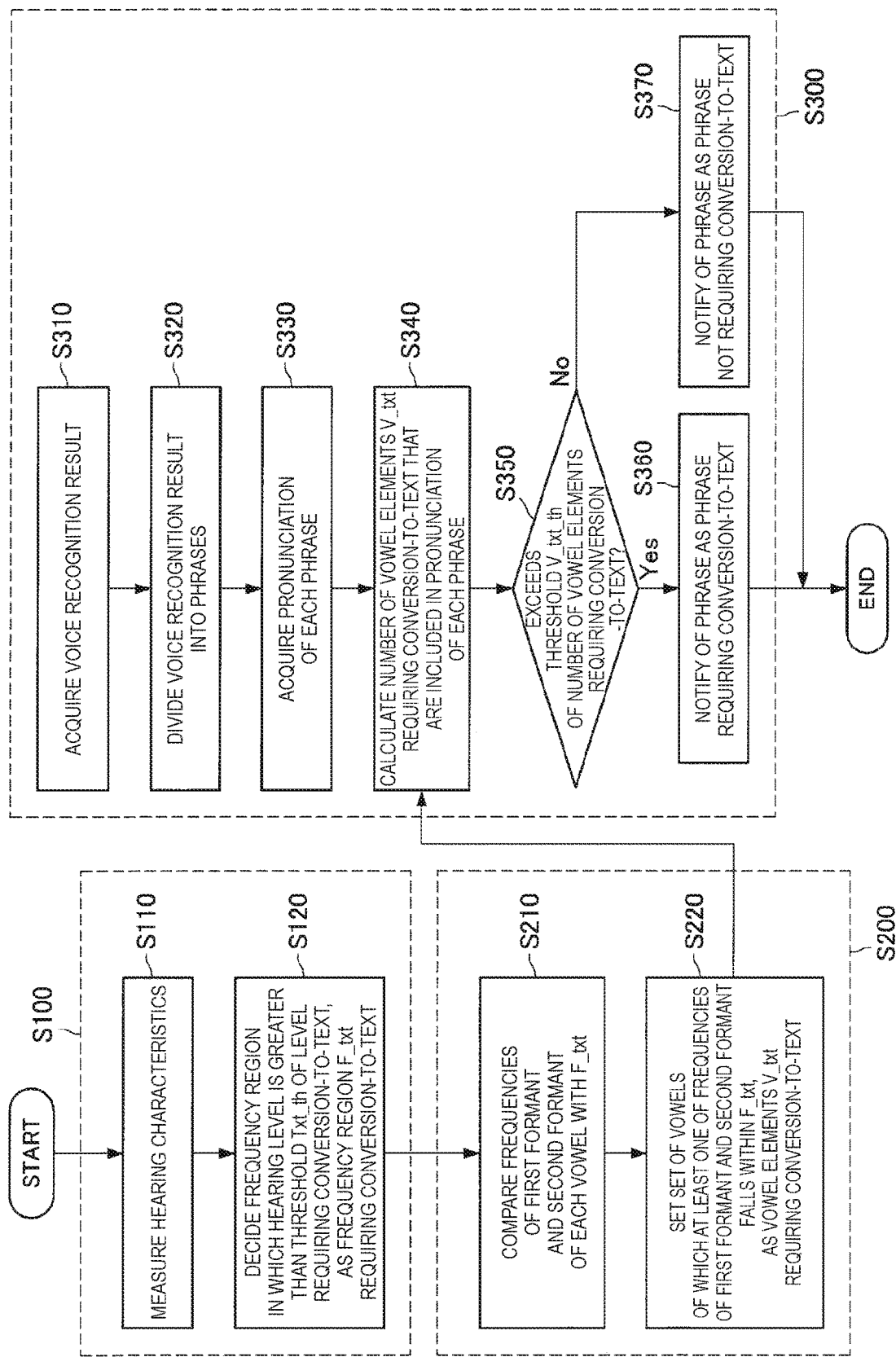
FIG. 8 is a flowchart illustrating an operation example of an information processing apparatus.

Now, an operation example of the information processing apparatus 10-1 will be described. FIG. 8 is a flowchart illustrating an operation example of the information processing apparatus 10-1. The flowchart in FIG. 8 merely illustrates an example of the operation of the information processing apparatus 10-1. Therefore, the operation of the information processing apparatus 10-1 is not limited to this example. First, the user U1's auditory characteristics are measured (step S110). Through this measurement, the acquisition unit 141 acquires information regarding the user U1's auditory characteristics. Note that as described above, auditory characteristics may be acquired by a technique other than measurement.

Subsequently, referring to the information regarding the user U1's auditory characteristics, the generation unit 142 decides a frequency region in which a hearing level is greater than the threshold Txt_th of the level requiring conversion-to-text, as the frequency region F_txt requiring conversion-to-text (step S120). Note that step S110 and step S120 are collectively referred to as step S100. Details of step S100 will be described later with reference to FIG. 9.

Subsequently, the generation unit 142 compares frequencies of the first formant and the second formant of each vowel with the frequency region F_txt requiring conversion-to-text (step S210). Then, the generation unit 142 sets a set of vowels of which at least one of the frequencies of the first formant and the second formant falls within the frequency region F_txt requiring conversion-to-text, as the vowel elements V_txt requiring conversion-to-text (S220). Note that step S210 and step S220 are collectively referred to as step S200. Details of step S200 will be described later with reference to FIG. 10.

Subsequently, the generation unit 142 acquires a voice recognition result (S310), and performs phrasal analysis on the voice recognition result, thereby dividing the voice recognition result in units of phrases (step S320). In addition, the generation unit 142 performs phonetic analysis on each phrase, thereby acquiring pronunciation of each phrase (step S330). Then, the generation unit 142 calculates the number of vowel elements V_txt requiring conversion-to-text that are included in the pronunciation of each phrase (step S340).

Subsequently, the generation unit 142 determines, for each phrase, whether the number of vowel elements V_txt requiring conversion-to-text exceeds the threshold V_txt_th of the number of vowel elements requiring conversion-to-text (step S350). If there is a phrase in which the number of vowel elements V_txt requiring conversion-to-text exceeds the threshold V_txt_th of the number of vowel elements requiring conversion-to-text, the generation unit 142 notifies an application of the phrase as a phrase requiring conversion-to-text (step S360).

On the other hand, if there is a phrase in which the number of vowel elements V_txt requiring conversion-to-text does not exceed the threshold V_txt_th of the number of vowel elements requiring conversion-to-text, the generation unit 142 notifies the application of the phrase as a phrase not requiring conversion-to-text (step S370). Note that steps S310 to S370 are collectively referred to as step S300.

Details of step S300 will be described later with reference to FIG. 11.

Figure 9:
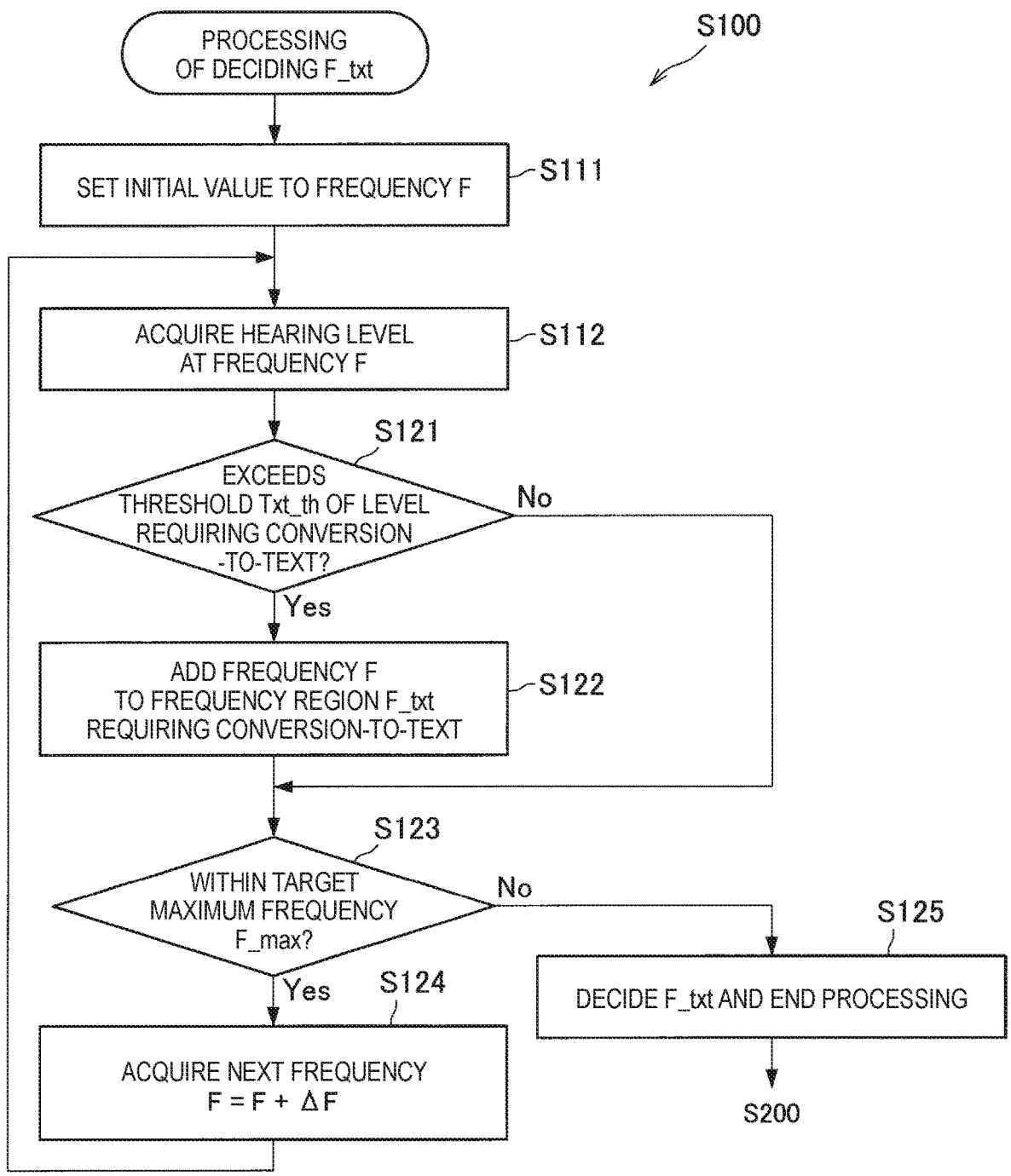
FIG. 9 illustrates an operation example of processing of deciding a frequency region requiring conversion-to-text.

FIG. 9 illustrates an operation example of processing of deciding the frequency region F_txt requiring conversion-to-text. As illustrated in FIG. 9, first, the generation unit 142 sets an initial value to a frequency F (step S111). Then, the generation unit 142 acquires a hearing level at the frequency F from the information regarding the user U1's auditory characteristics (step S112). The generation unit 142 determines whether the hearing level at the frequency F exceeds the threshold Txt_th of the level requiring conversion-to-text (step S121).

Subsequently, in the case where the hearing level at the frequency F exceeds the threshold Txt_th of the level requiring conversion-to-text ("Yes" in step S121), the generation unit 142 adds the frequency F to the frequency region F_txt requiring conversion-to-text, and shifts the operation to step S123. On the other hand, in the case where the hearing level at the frequency F does not exceed the threshold Txt_th of the level requiring conversion-to-text ("No" in step S121), the generation unit 142 decides the frequency region F_txt requiring conversion-to-text and ends the processing (step S125). After that, the operation is shifted to step S200.

Subsequently, the generation unit 142 determines whether the frequency F is within a target maximum frequency F_max (step S123). Then, in the case where the frequency F is within the target maximum frequency F_max ("Yes" in step S123), the generation unit 142 acquires the next frequency (step S124), and shifts the operation to step S112. On the other hand, in the case where the frequency F is within the range of the target maximum frequency F_max ("No" in step S123), the generation unit 124 decides the frequency region F_txt requiring conversion-to-text and ends the processing (step S125). After that, the operation is shifted to processing of searching for vowel elements V_txt_th requiring conversion-to-text.

Figure 10:
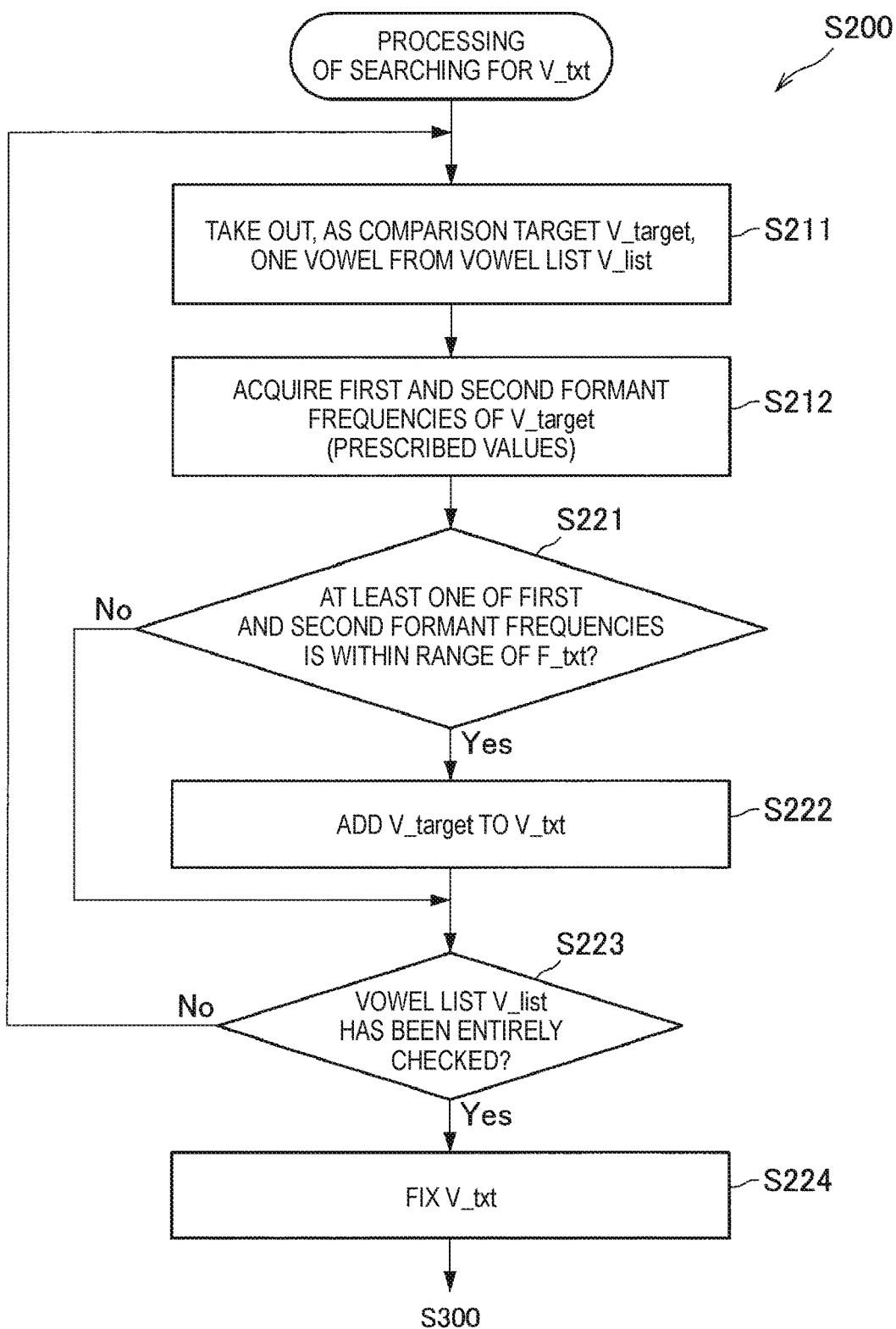
FIG. 10 illustrates an operation example of processing of searching for vowel elements requiring conversion-to-text.

FIG. 10 illustrates an operation example of processing of searching for vowel elements V_txt_th requiring conversion-to-text. As illustrated in FIG. 10, first, the generation unit 142 takes out, as a comparison target V_target, one vowel from a vowel list V_list prepared in advance (step S211). Then, the generation unit 142 acquires a first formant frequency and a second formant frequency of the comparison target V_target (step S212), and determines whether at least one of the first formant frequency and the second formant frequency of the comparison target V_target is within the range of the frequency region F_txt requiring conversion-to-text (step S221).

In the case of determining that both the first formant frequency and the second formant frequency of the comparison target V_target are outside the range of the frequency region F_txt requiring conversion-to-text ("No" in step S221), the generation unit 142 shifts the operation to step S223. On the other hand, in the case of determining that at least one of the first formant frequency and the second formant frequency of the comparison target V_target is within the range of the frequency region F_txt requiring conversion-to-text ("Yes" in step S221), the generation unit 142 adds the comparison target V_target to the vowel elements V_txt requiring conversion-to-text (step S222), and shifts the operation to step S223.

Subsequently, the generation unit 142 determines whether the vowel list V_list has been entirely checked (step S223). In the case where part or the whole of the vowel list V_list has not been checked ("No" in step S223), the generation unit 142 shifts the operation to step S211. On the other hand, in the case where the whole of the vowel list V_list has been checked ("No" in step SS223), the generation unit 142 fixes the vowel elements V_txt requiring conversion-to-text (step S224).

Figure 11:
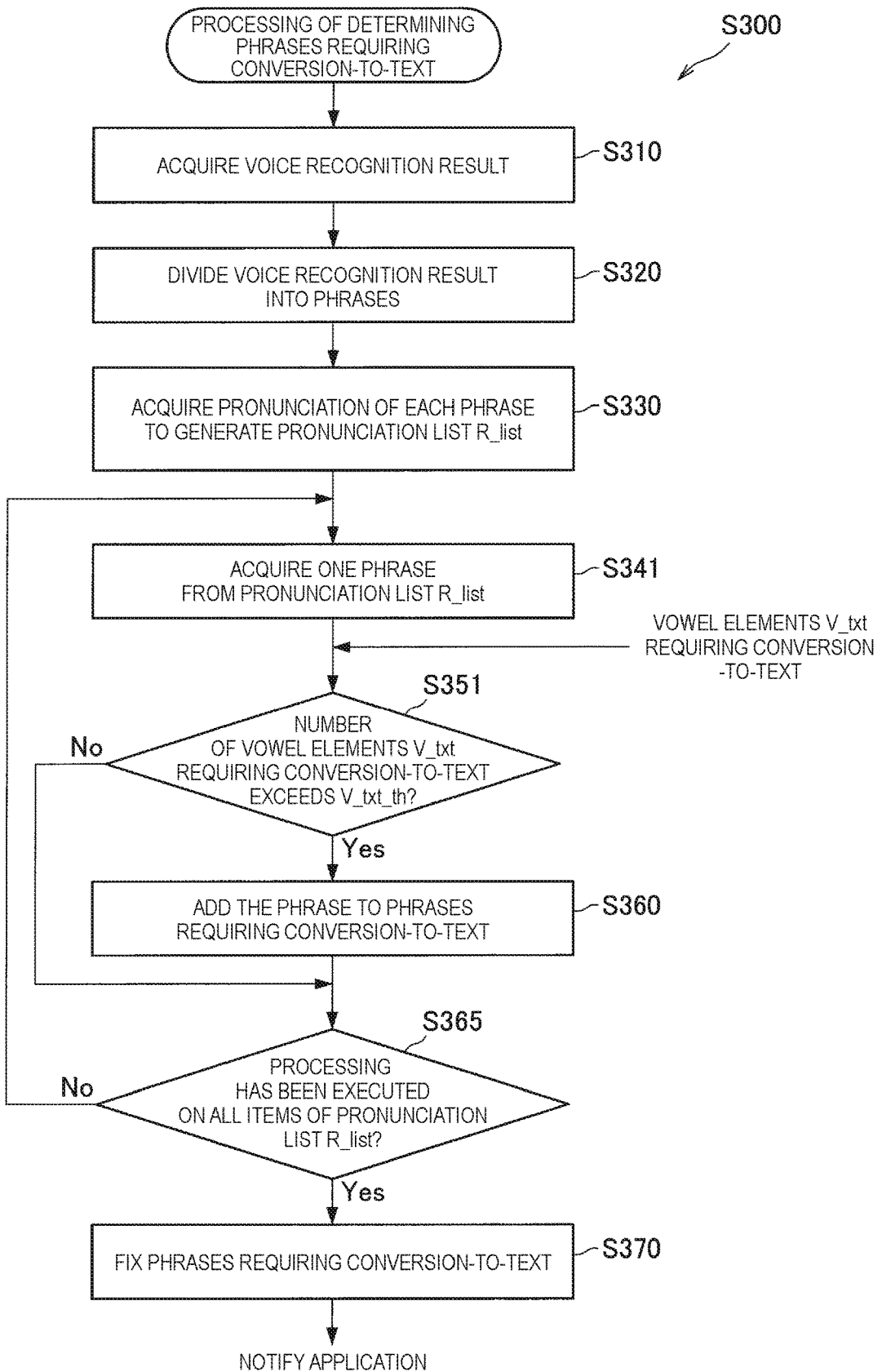
FIG. 11 illustrates an operation example of processing of determining phrases requiring conversion-to-text.

FIG. 11 illustrates an operation example of processing of determining phrases requiring conversion-to-text. First, the generation unit 142 acquires a result of voice recognition performed on spoken voice (step S310). Then, the generation unit 142 divides the voice recognition result into phrases (step S320), and acquires pronunciation of each phrase to generate a pronunciation list R_list (step S330). The generation unit 142 acquires one phrase from the pronunciation list R_list (step S341), and determines whether the number of vowel elements V_txt requiring conversion-to-text exceeds the threshold V_txt_th of the number of vowel elements requiring conversion-to-text (step S351).

In the case where the number of vowel elements V_txt requiring conversion-to-text exceeds the threshold V_txt_th of the number of vowel elements requiring conversion-to-text ("No" in step S351), the generation unit 142 shifts the operation to step S365. On the other hand, in the case where the number of vowel elements V_txt requiring conversion-to-text does not exceed the threshold V_txt_th of the number of vowel elements requiring conversion-to-text ("Yes" in step S351), the generation unit 142 adds the phrase to phrases requiring conversion-to-text (step S360), and shifts the operation to step S365.

Subsequently, the generation unit 142 determines whether the processing has been executed on all the items of the pronunciation list R_list (step S365). Then, in the case where the processing has not been executed on some or all of the items of the pronunciation list R_list ("No" in step S365), the generation unit 142 shifts the operation to step S341. On the other hand, in the case where the processing has been executed on all of the items of the pronunciation list R_list ("Yes" in step S365), the generation unit 141 fixes the phrases requiring conversion-to-text (step S370), and notifies the application of the phrases requiring conversion-to-text.

1.5. Various Modification Examples

Now, various modification examples of the information processing apparatus 10-1 will be described. FIG. 12 shows an example of a frequency band (passband) of voice spoken in each language. FIG. 12 shows passbands of Japanese, English, Italian, German, and Russian. As is understood from FIG. 12, the passband differs depending on the language used. Hence, it is acceptable as long as an auditory level corresponding to this passband is acquired; thus, a test related to auditory sense may be performed for a frequency region corresponding to this passband.

FIG. 13 shows examples of the first formant and the second formant in Japanese. In addition, FIG. 14 shows examples of the first formant and the second formant in English. According to FIGS. 13 and 14, it is understood that there is little difference in the first formant frequency and the second formant frequency between Japanese and English. As is understood from the example of English, it seems that the same applies to the relationship between Japanese and other foreign languages. Hence, the present embodiment is applicable to voice spoken in every foreign language.

In addition, the above description is given on an example in which information regarding the user U1's auditory characteristics is acquired on the basis of a result of a test related to the user U1's auditory sense, which is performed in advance, but the information regarding the user U1's auditory characteristics may be acquired in any manner.

For example, the acquisition unit 141 may acquire information regarding the user U1's auditory characteristics on the basis of attribute information of the user U1. The attribute information may be predetermined information (e.g., age, language used, sex, or the like) that may influence auditory characteristics. If information regarding auditory characteristics is associated with attribute information in advance, the acquisition unit 141 can acquire information regarding auditory characteristics that corresponds to the attribute information of the user U1, on the basis of the association and information regarding auditory characteristics.

Alternatively, the acquisition unit 141 may acquire information regarding the user U1's auditory characteristics that is registered in advance. The information regarding the user U1's auditory characteristics may be registered in the storage unit 160, or may be registered in a server (not illustrated) or the like. Moreover, in the case where information regarding auditory characteristics is registered for each user, the information regarding the user U1's auditory characteristics may be acquired from the information regarding auditory characteristics for each user. Alternatively, information regarding a typical user's auditory characteristics may be acquired as the information regarding the user U1's auditory characteristics.

Alternatively, since it is assumed that difficulty in hearing sound information may change in accordance with an environment where the user U1 is present, the acquisition unit 141 may acquire information regarding the user's auditory characteristics on the basis of information regarding the environment where the user U1 is present. For example, it is presumed that larger environmental noise leads to greater difficulty in the user U1 catching sound information. Therefore, the generation unit 142 may change an auditory level so that the auditory level greatly decreases as noise in the environment where the user U1 is present becomes larger.

Figure 15:
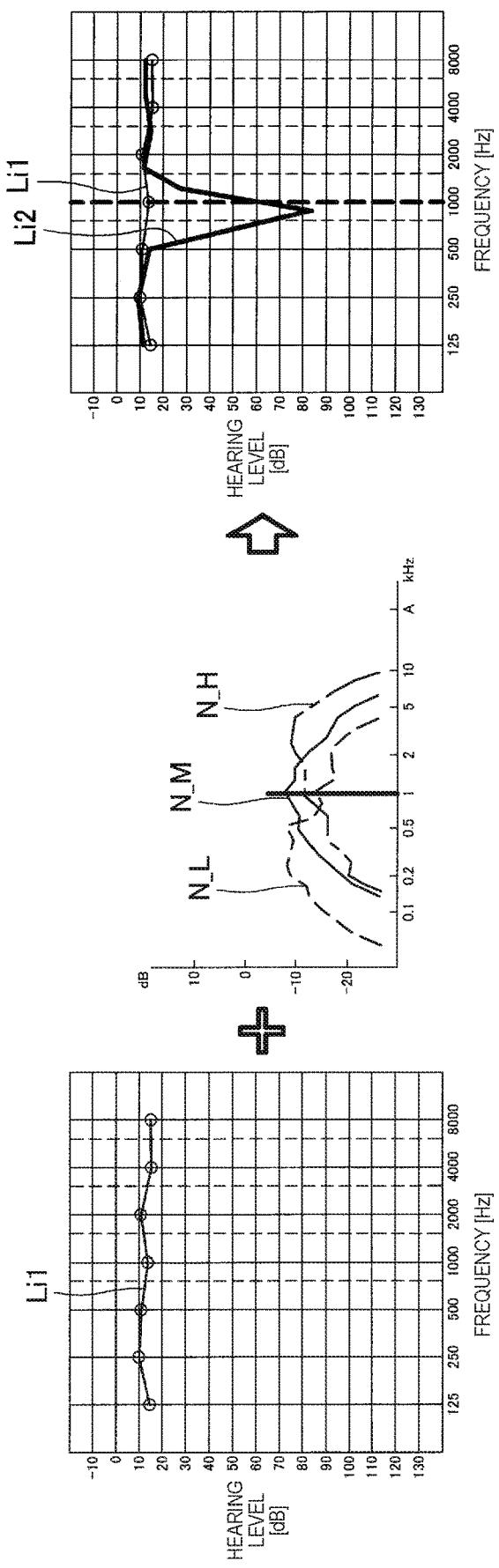
FIG. 15 illustrates an example in which an auditory level is changed in accordance with environmental noise.

FIG. 15 illustrates an example in which an auditory level is changed in accordance with environmental noise. According to FIG. 15, information Li1 regarding the user U1's auditory characteristics in a normal case is shown. In addition, as examples of environmental noise, there are shown noise N_L in a running train, noise N_M in a zoo, and noise N_H during dishwashing. In the case where the user U1 is present in these environments, it is preferable to assume that a hearing level at the main frequency of the environmental noise decreases, and change an auditory level so that the hearing level at the main frequency decreases. FIG. 15 shows information Li2 regarding changed auditory characteristics.

Figure 16:
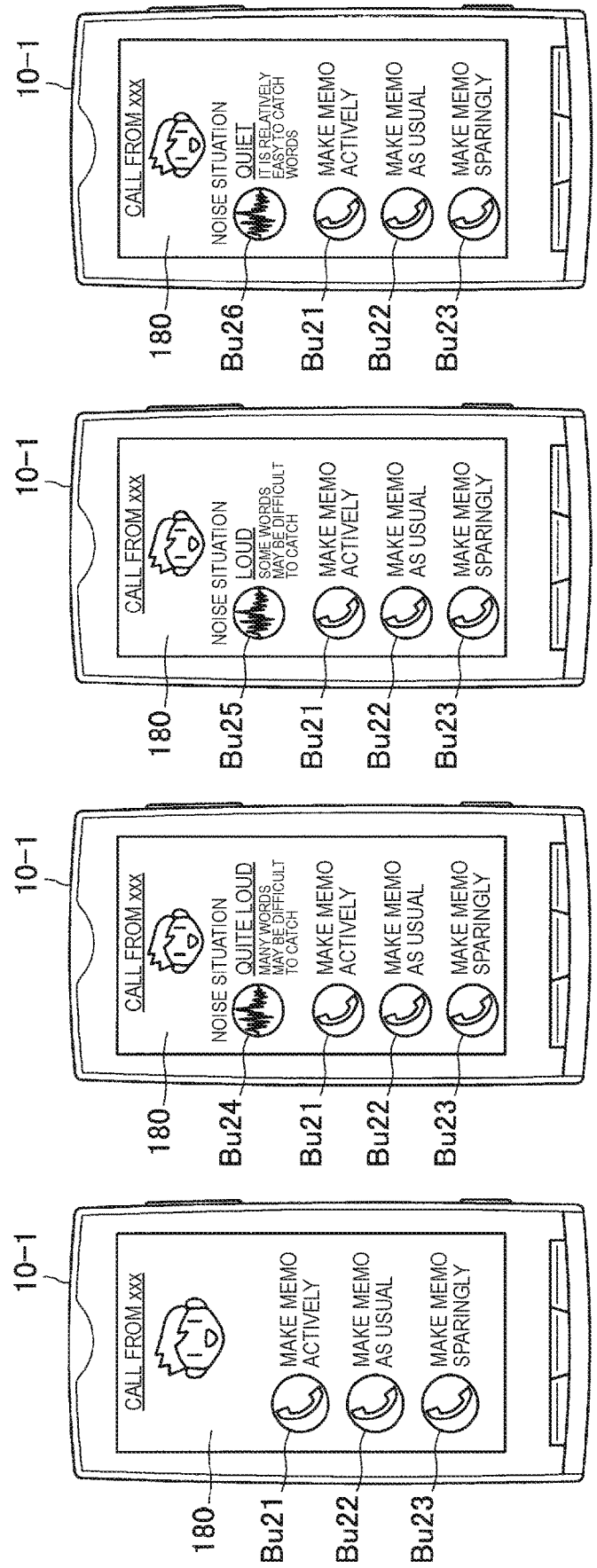
FIG. 16 illustrates a display example of information regarding environment.

In addition, information regarding environment may be displayed by the display unit 180. This enables the user U1 to easily grasp the degree of difficulty in catching voice spoken by the user 2. Moreover, the user U1 who has viewed the information regarding environment may be able to select the degree to which the information processing apparatus 10-1 performs conversion-to-text. FIG. 16 illustrates a display example of information regarding environment.

As illustrated in FIG. 16, the display unit 180 displays a button Bu21 for selecting a relatively large amount of conversion-to-text, a button Bu22 for selecting a middle amount of conversion-to-text, and a button Bu23 for selecting a relatively small amount of conversion-to-text. In addition, the display unit 180 displays, as the information regarding environment, information Bu24 indicating large environmental noise, information Bu25 indicating middle environmental noise, and information Bu26 indicating small environmental noise.

Alternatively, since it is assumed that difficulty in hearing sound information may change in accordance with activity information of the user U1, the acquisition unit 141 may acquire information regarding the user's auditory characteristics on the basis of the activity information of the user U1. For example, difficulty in hearing sound information may differ depending on whether the user U1 is sitting, standing still, walking, running, taking a train, or driving a car. Hence, the acquisition unit 141 may acquire information regarding auditory characteristics that corresponds to the activity information of the user U1.

Figure 17:
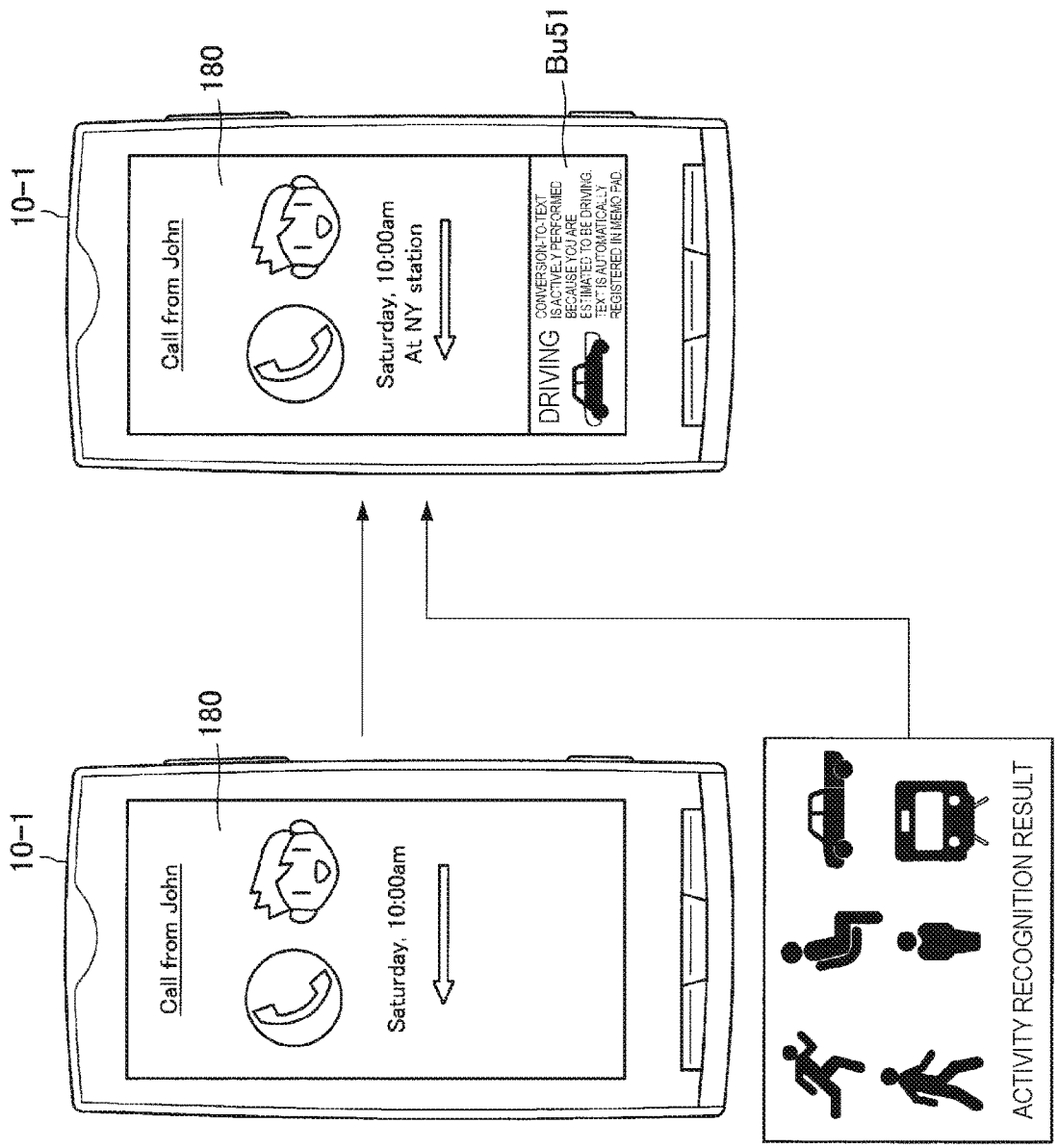
FIG. 17 illustrates an example in which an auditory level is changed in accordance with activity information.

FIG. 17 illustrates an example in which an auditory level is changed in accordance with activity information. According to FIG. 17, the following case is assumed: various types of activity information are shown as examples of an activity recognition result, and activity information indicating driving of a car is acquired by the acquisition unit 141. It is presumed that, during driving of a car, sound information is more difficult to catch than in normal time. Hence, the acquisition unit 141 preferably changes an auditory level so that a hearing level decreases. In FIG. 17, a screen Bu51 indicating that conversion-to-text is actively performed is displayed.

Displaying the degree to which conversion-to-text is performed in this manner enables the user U1 to easily grasp the degree to which a voice recognition result is converted to text. As illustrated in FIG. 17, the activity information "driving" of the user U1 may be displayed by the display unit 180. This enables the user U1 to easily grasp the degree of difficulty in catching voice spoken by the user 2. Moreover, the user U1 who has viewed the activity information may be able to select the degree to which the information processing apparatus 10-1 performs conversion-to-text.

Alternatively, since it is assumed that difficulty in hearing sound information may change in accordance with biological information of the user U1, the acquisition unit 141 may acquire information regarding the user's auditory characteristics on the basis of the biological information of the user U1. For example, difficulty in hearing sound information may differ depending on whether the user U1 is doing exercise or at rest. Hence, the acquisition unit 141 may acquire information regarding auditory characteristics that corresponds to the biological information of the user U1.

Figure 18:
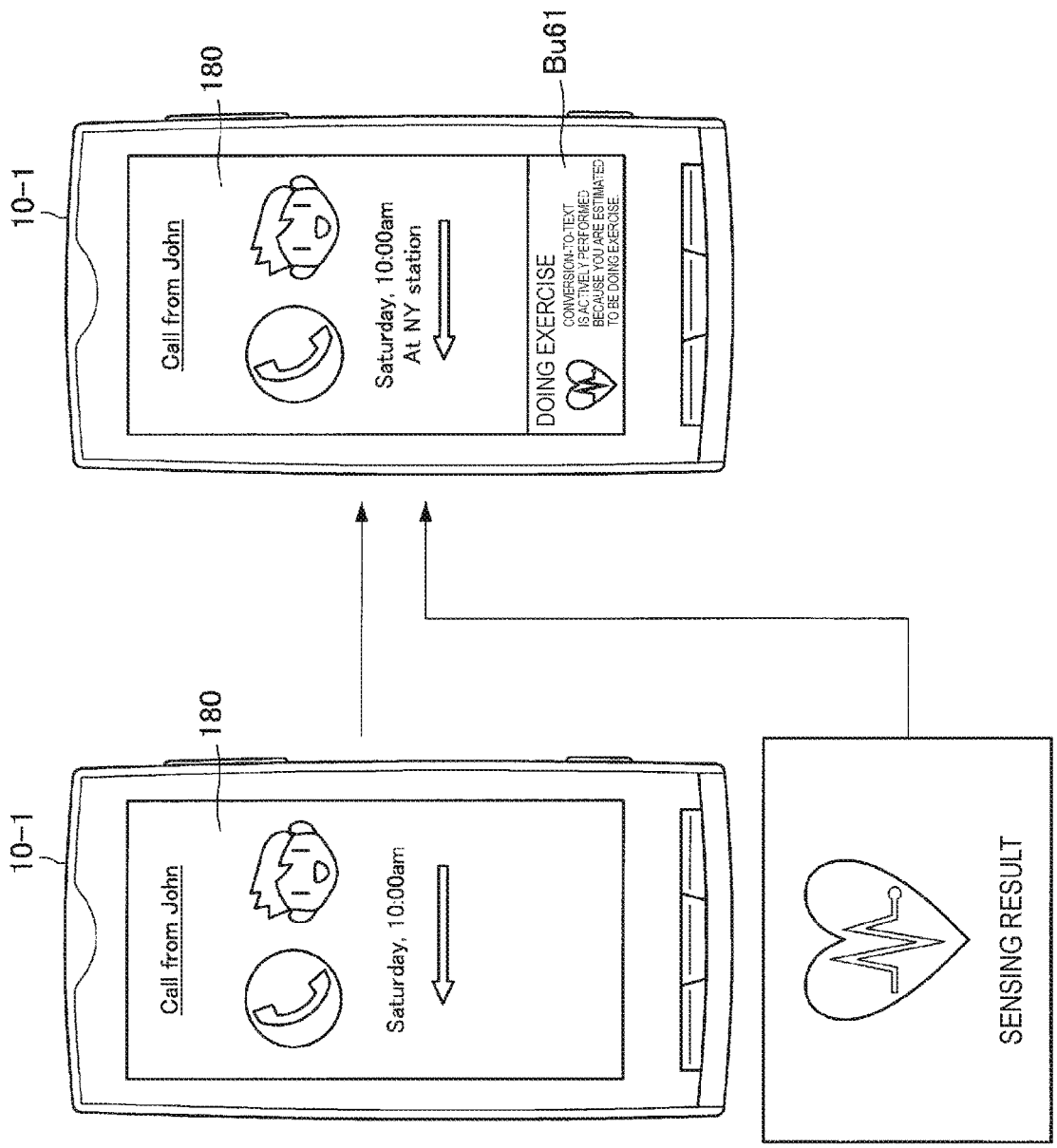
FIG. 18 illustrates an example in which an auditory level is changed in accordance with biological information.

FIG. 18 illustrates an example in which an auditory level is changed in accordance with biological information. According to FIG. 18, the following case is assumed: a heart rate is shown as an example of a sensing result, and biological information indicating exercise is acquired by the acquisition unit 141. It is presumed that, during exercise, sound information is more difficult to catch than in normal time. Hence, the acquisition unit 141 preferably changes an auditory level so that a hearing level decreases. In FIG. 18, a screen Bu61 indicating that conversion-to-text is actively performed is displayed.

Displaying the degree to which conversion-to-text is performed in this manner enables the user U1 to easily grasp the degree to which a voice recognition result is converted to text. As illustrated in FIG. 18, the biological information "doing exercise" of the user U1 may be displayed by the display unit 180. This enables the user U1 to easily grasp the degree of difficulty in catching voice spoken by the user 2. Moreover, the user U1 who has viewed the activity information may be able to select the degree to which the information processing apparatus 10-1 performs conversion-to-text.

In addition, the above description is given on a scene where the user U1 and the user U2 have a conversation by a telephone function of the information processing apparatus 10-1 and the information processing apparatus 10-2, but a scene to which the technology of the present disclosure is applied is not limited to this scene. For example, the technology of the present disclosure may be widely applied to the field of health care. For example, in a scene where a patient gets dental treatment by a dentist, sound of dental treatment may prevent the dentist and the patient from catching each other's voice. The technology of the present disclosure may be applied to such a scene of dental treatment for a patient performed by a dentist.

Figure 19:
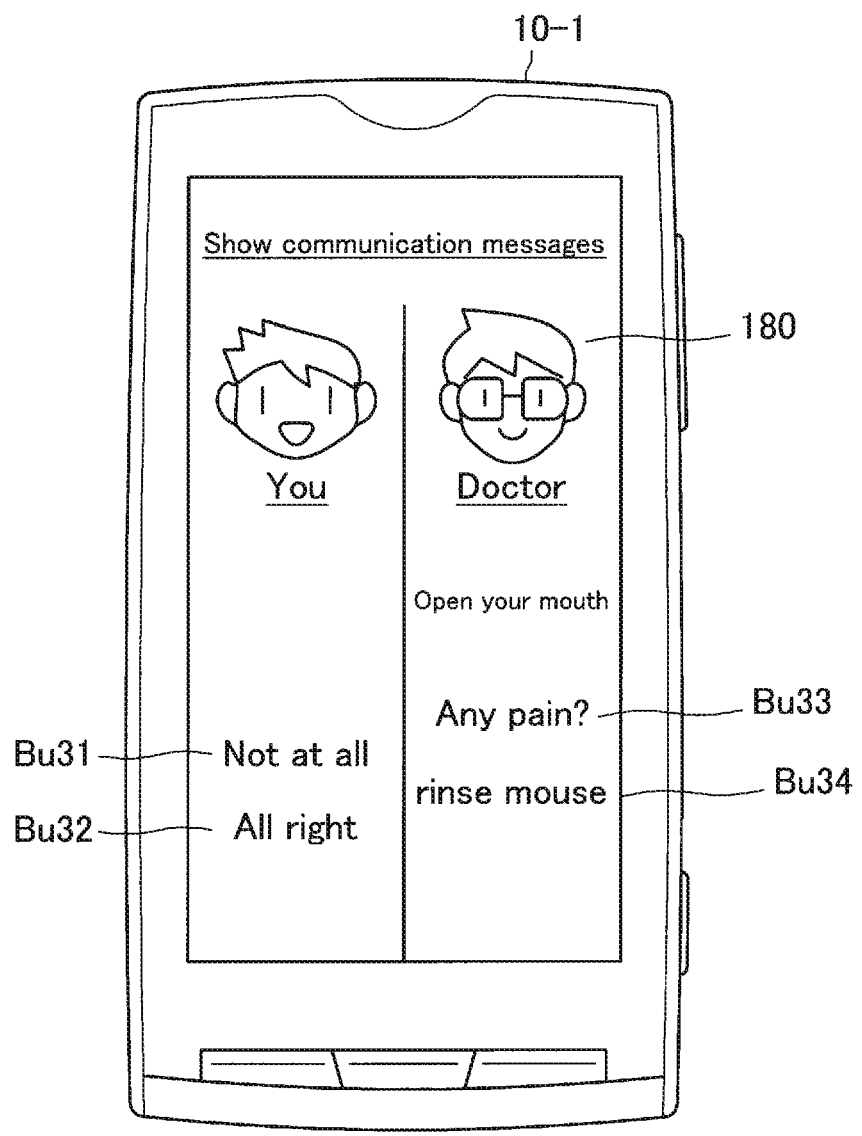
FIG. 19 is a diagram for describing a case where the technology of the present disclosure is applied to a scene of dental treatment.

FIG. 19 is a diagram for describing a case where the technology of the present disclosure is applied to a scene of dental treatment. According to FIG. 19, examples of phrases converted to text from a voice recognition result of voice spoken by a patient are shown as a phrase Bu31 and a phrase Bu32. A dentist can utilize a result of seeing the phrase Bu31 and the phrase Bu32 for dental treatment. In addition, examples of phrases converted to text from a voice recognition result of voice spoken by the dentist are shown as a phrase Bu33 and a phrase Bu34. The patient can answer to the dentist in regard to a result of seeing the phrase Bu33 and the phrase Bu34.

In addition, the above description is given mainly on a case where output text data is displayed as output information, but displayed information may include an image, a stamp, and the like in addition to output text data. For example, in the case where a predetermined noun is included in output text data, the output unit 143 may output an image or a stamp corresponding to the noun, and the display unit 180 may display the image or the stamp. Such a function can enhance the speed of the user U1 understanding what the user U2 speaks.

Figure 20:
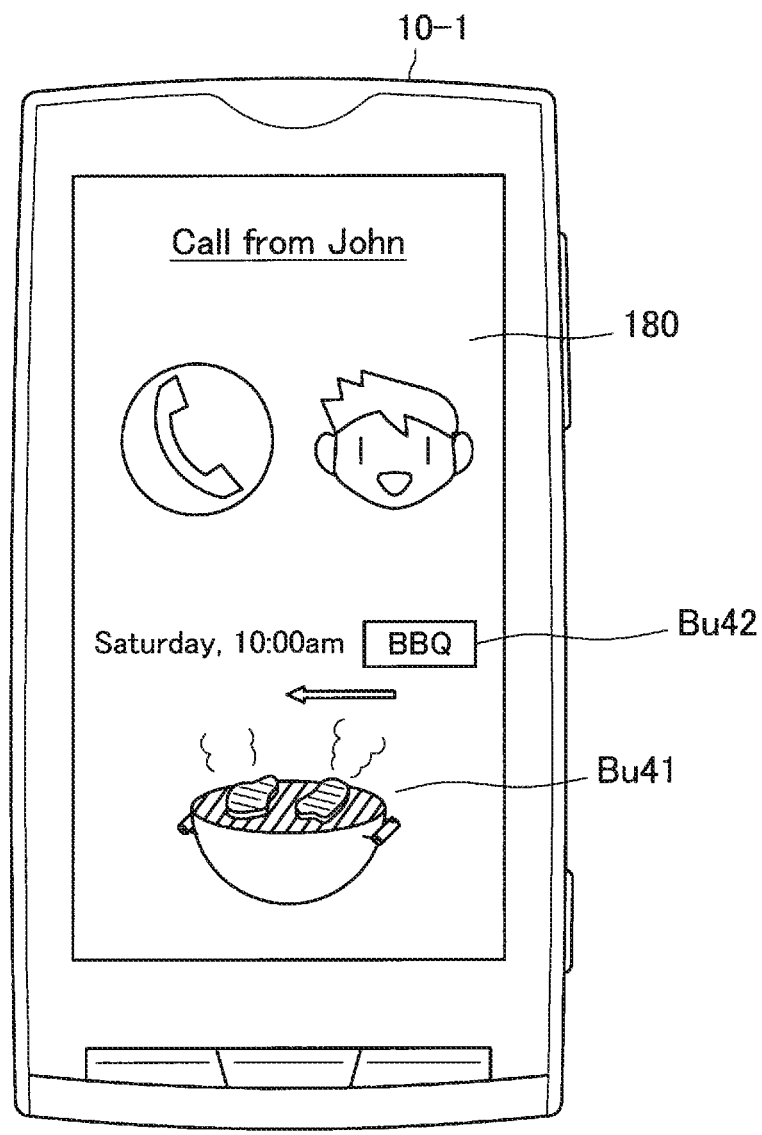
FIG. 20 is a diagram for describing a case where a predetermined noun is included in output text data.

FIG. 20 is a diagram for describing a case where a predetermined noun is included in output text data. As illustrated in FIG. 20, assume that "barbeque (BBQ)" is included in output text data. At this time, as illustrated in FIG. 20, the output 143 may output an image Bu41 and a stamp Bu42 corresponding to "barbeque (BBQ)", and the display unit 180 may display the image Bu41 and the stamp Bu42.

In addition, the above description is given mainly on an example in which output information is output only once, but the output unit 143 may output output information again in the case where a predetermined condition is satisfied after the output information is output. Here, the predetermined condition is not particularly limited. Hence, the predetermined condition may be a condition that the user U1 has carried out a predetermined operation, or may be elapse of predetermined time from the end of a phone conversation. Description will be continued taking as an example a case where the predetermined condition is elapse of predetermined time.

Figure 21:
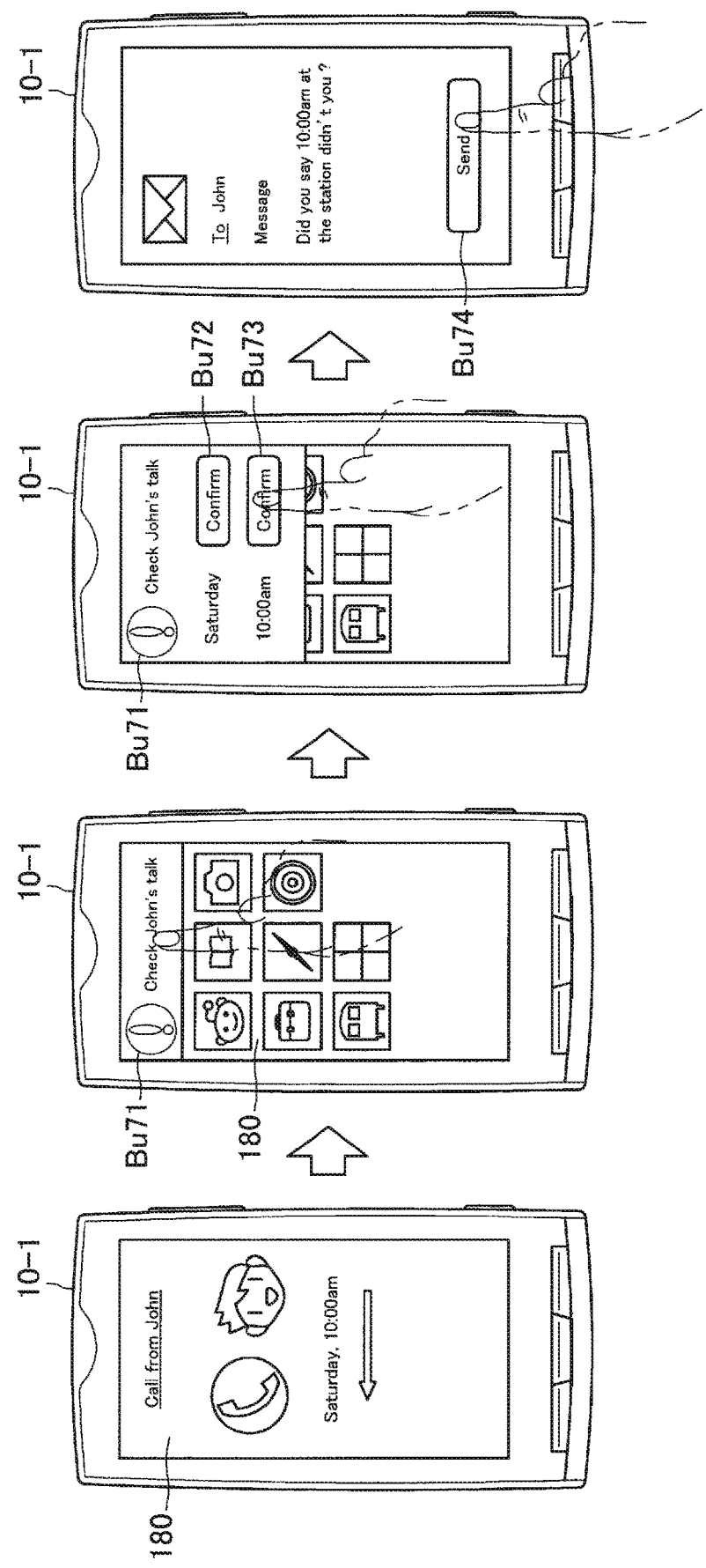
FIG. 21 is a diagram for describing an example in which output information is output again.

FIG. 21 is a diagram for describing an example in which output information is output again. According to FIG. 21, "10:00 am" and "Saturday" are converted to text from a result of voice recognition performed on spoken voice of the user U2, who is the phone conversation partner, and these are displayed as output text data by the display unit 180. A notification screen Bu71 is displayed after predetermined time has elapsed from the end of the phone conversation, and when the user U1 selects the notification screen Bu71, buttons Bu72 and Bu73 for selecting reconfirmation of "10:00 am" and "Saturday", respectively, may be displayed.

As illustrated in FIG. 21, for example, when the user U1 presses the button Bu73 for selecting reconfirmation of "10:00 am", the generation Bu 142 may automatically start up a mail application to ask the user U2, who is the phone conversation partner, about "10:00 am" for reconfirmation. Then, the display unit 180 may display a message asking whether the user U2 has said "10:00 am" and a button Bu74 for transmitting the message.

In addition, the above description is given on an example in which output information is displayed in the information processing apparatus 10-1, which receives voice spoken by the user U2, but the output information may be displayed by the information processing apparatus 10-2 used by the user U2 who is speaking. This enables the user U2 to grasp sound that is difficult for the user U1 to catch, utilize the result of grasp when speaking again, and correct text. A result of text correction is preferably transmitted to the information processing apparatus 10-1 of the user U1, and displayed in the information processing apparatus 10-1.

Figure 22:
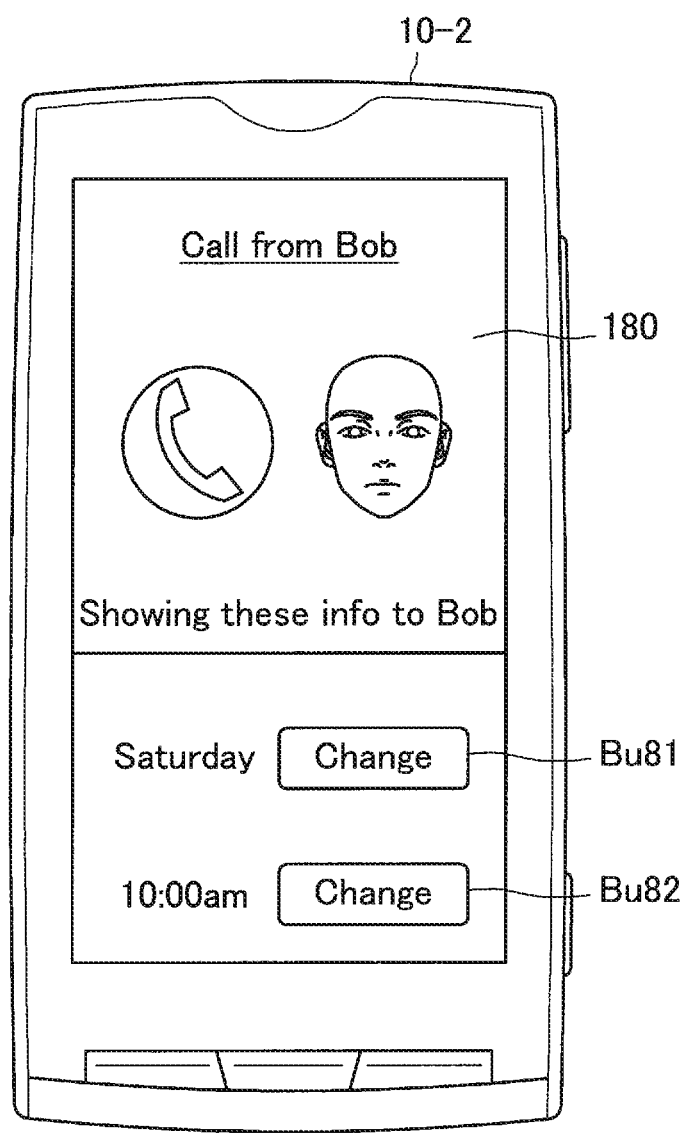
FIG. 22 illustrates a display example of output information by an information processing apparatus of a user who is speaking.

FIG. 22 illustrates a display example of output information by the information processing apparatus 10-2 of the user U2 who is speaking. According to FIG. 22, "10:00 am" and "Saturday" are converted to text from a result of voice recognition performed on spoken voice of the user U2 who is speaking, and these are displayed as output text data by the display unit 180 in the information processing apparatus 10-2. In addition, buttons Bu81 and Bu82 for selecting correction of "10:00 am" and "Saturday", respectively, are displayed.

Figure 23:
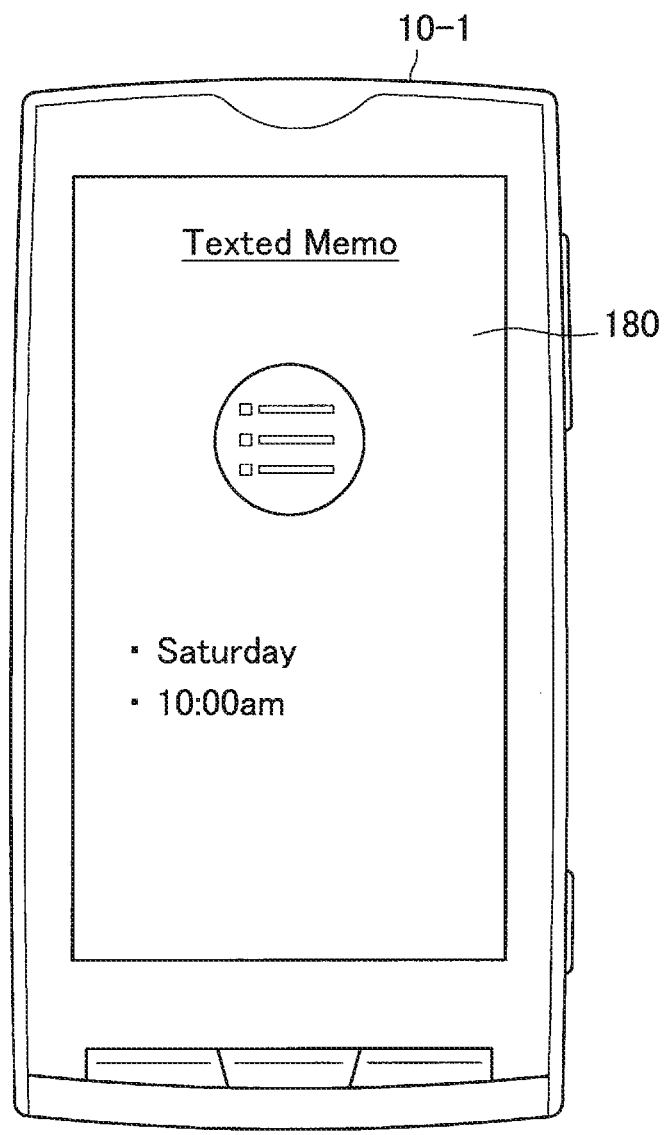
FIG. 23 illustrates an example of output information displayed after a phone conversation by a telephone function ends.

In addition, the above description is given on output information that is displayed while the user U1 and the user U2 are having a phone conversation by a telephone function of the information processing apparatus 10-1 and the information processing apparatus 10-2, but output information may be displayed after the phone conversation by the telephone function ends. That is, output information may be used as a complementary memo for the user U1 to later see details of a phone conversation by a telephone function with the user U2. FIG. 23 illustrates an example of output information displayed after a phone conversation by a telephone function ends.

In addition, the above description is given taking as an example a case where the information processing apparatus 10-1 and the information processing apparatus 10-2 are each a smartphone, but the information processing apparatus 10-1 and the information processing apparatus 10-2 are not particularly limited in form.

For example, the information processing apparatus 10-1 may be a head mount display (HMD). FIG. 24 illustrates a case where the information processing apparatus 10-1 is a HMD. FIG. 24 illustrates the display unit 180 implemented by a HMD.

In addition, the above description is given mainly on a case where the form of output information is image information generated on the basis of output text data, but the form of output information is not limited to image information. For example, output information may include at least one of sound information, image information, and vibration information generated on the basis of output text data. FIG. 25 is a diagram for describing a case where output information includes sound information generated on the basis of output text data. According to FIG. 25, the user U1 wears the audio output unit 170.

The audio output unit 170 may output sound information generated on the basis of output text data. This enables the user U1 to grasp details of output text data through sound information. Note that it may be difficult for the user U1 to listen to sound information generated on the basis of output text data, while having a conversation with the user U2 by a telephone function. Therefore, this sound information is preferably output at a timing of interruption of the conversation by a telephone function with the user U2.

In addition, the above description is given on an example in which a result of voice recognition performed on spoken voice of the user U2, who is the phone conversation partner of the user U1, is used as text data, but other text data may be used instead of a voice recognition result. That is, text data based on content may be used. For example, the following scene is assumed: by playing video data, the user U1 listens to sound information accompanying video while viewing the video. In this scene, it is predicted that a success rate of catching sound information differs depending on the user's auditory characteristics. Hence, a result of voice recognition performed on sound information accompanying video data may be used.

Figure 26:
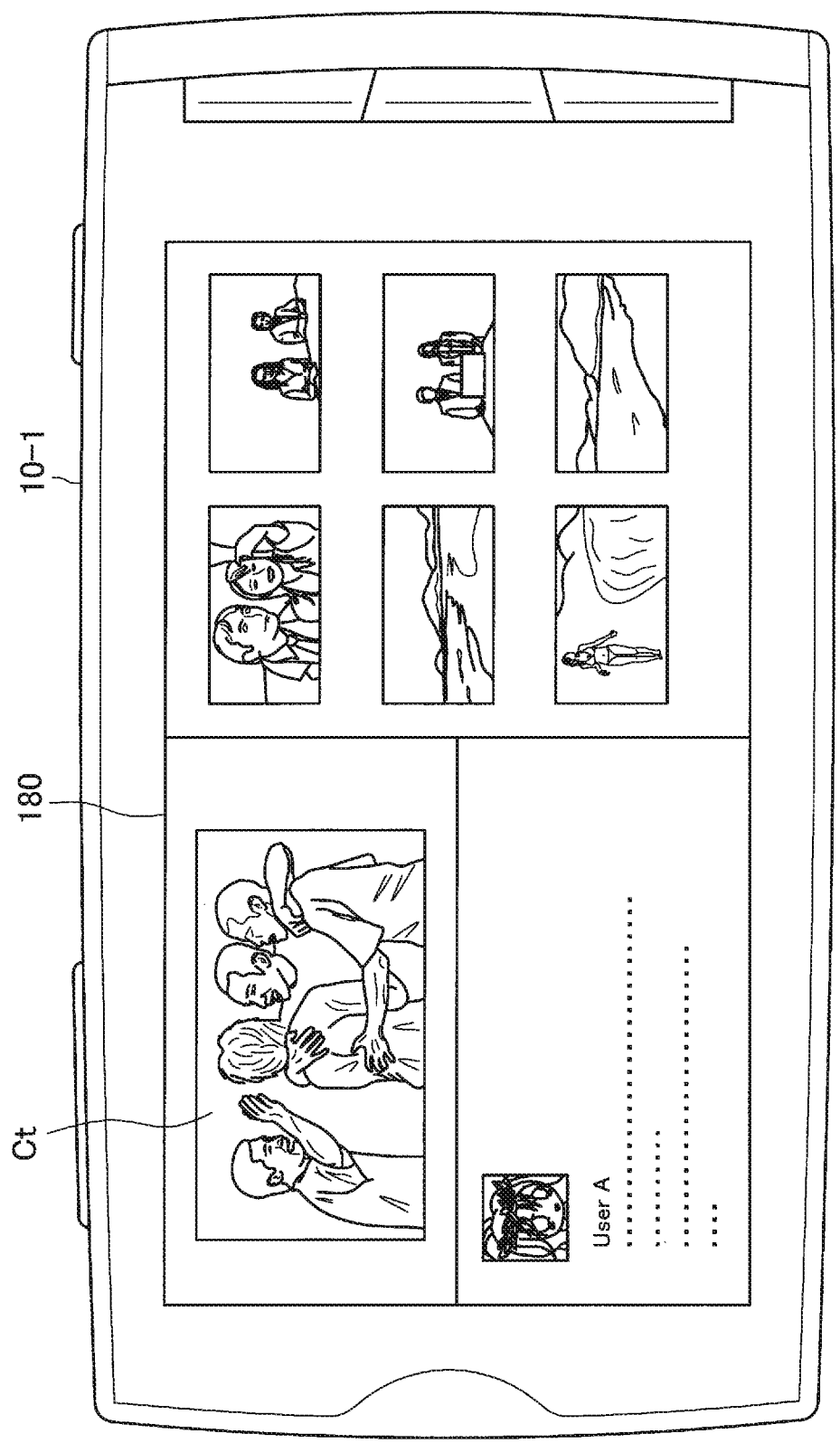
FIG. 26 illustrates a display example of video accompanied by sound information.

FIG. 26 illustrates a display example of video accompanied by sound information. According to FIG. 26, video Ct is played and displayed. In addition, sound information accompanying the video Ct is played and output. Hence, in the information processing apparatus 10-1, the generation unit 142 may perform voice recognition processing on the sound information accompanying the video Ct, and use a voice recognition result obtained by the voice recognition processing as text data. Alternatively, a caption or the like accompanying video may be used as text data.

Moreover, the generation unit 142 may make granularity of output text data lower than granularity of a voice recognition result. More specifically, the generation unit 142 may make granularity of output text data lower than granularity of a voice recognition result by excluding a predetermined word from the voice recognition result. For example, in the case where "Hi John, we need to meet at the station around 10:00 am" is obtained as a voice recognition result, this voice recognition result is broken down into "Hi John," "we need to meet" "at the station" "around 10:00 am".

The generation unit 142 may exclude an unnecessary word determined for each language from each phrase obtained in this manner. For example, in the case of English, the unnecessary word may be a preposition or emphatic expression. For example, since "need to", "at", and "around" are prepositions, these may be excluded and "Hi John," "we meet" "the station" "10:00 am" may be displayed. This enables the user to view information with higher necessity.

1.6. Hardware Configuration Example

Figure 27:
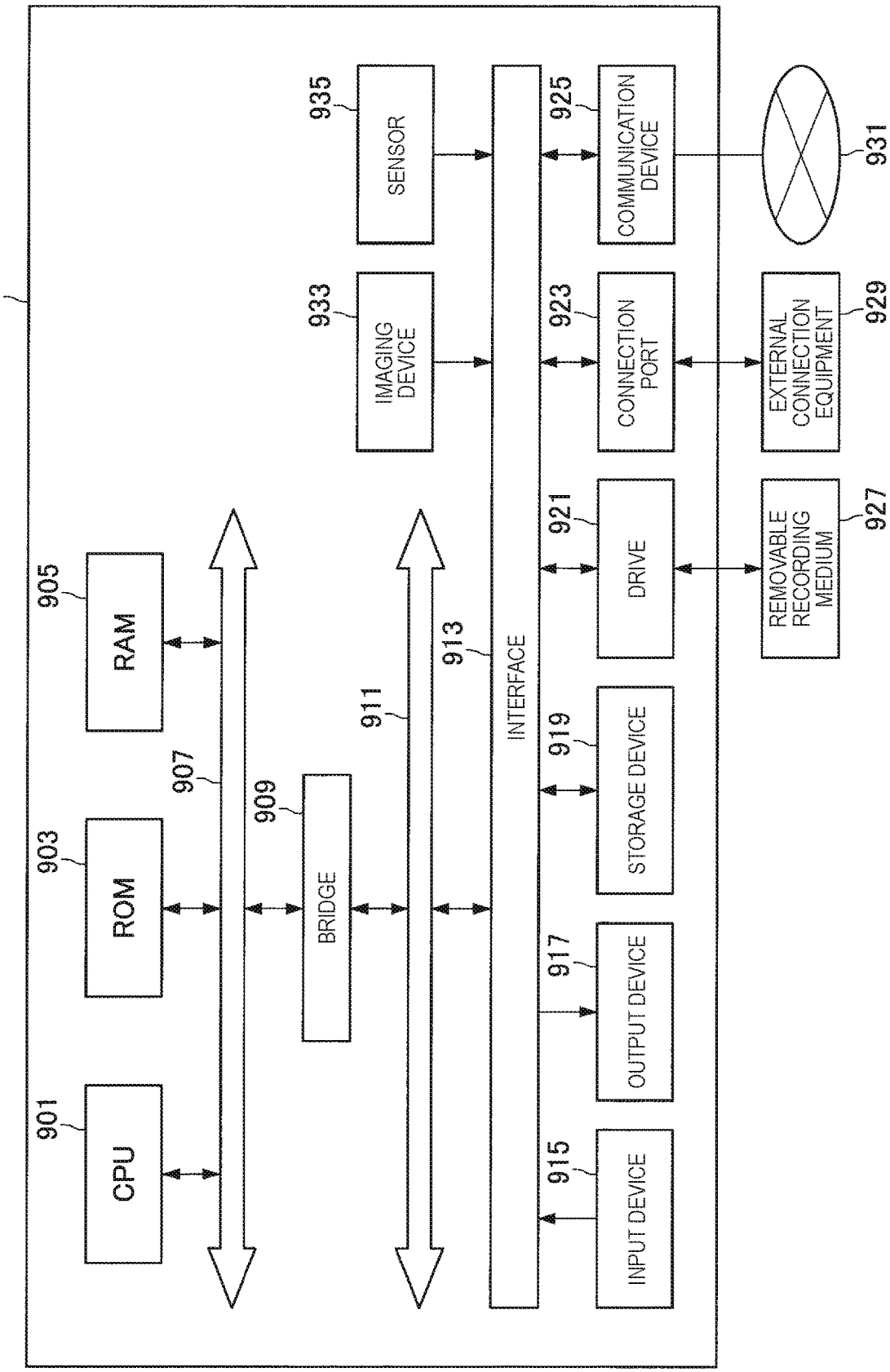
FIG. 27 is a block diagram illustrating a hardware configuration example of an information processing apparatus.

Next, with reference to FIG. 27, a hardware configuration of the information processing apparatus 10 according to the embodiment of the present disclosure will be described. FIG. 27 is a block diagram illustrating the hardware configuration example of the information processing apparatus 10 according to the embodiment of the present disclosure.

As illustrated in FIG. 27, the information processing apparatus 10 includes a central processing unit (CPU) 901, a read only memory (ROM) 903, and a random access memory (RAM) 905. In addition, the information processing apparatus 10 may include a host bus 907, a bridge 909, an external bus 911, an interface 913, an input device 915, an output device 917, a storage device 919, a drive 921, a connection port 923, and a communication device 925. Moreover, the information processing apparatus 10 may include an imaging device 933 and a sensor 935, as necessary. The information processing apparatus 10 may include a processing circuit such as a digital signal processor (DSP) or an application specific integrated circuit (ASIC), alternatively or in addition to the CPU 901.

The CPU 901 functions as an arithmetic processing device and a control device, and controls the overall operation or a part of the operation of the information processing apparatus 10 according to various programs recorded in the ROM 903, the RAM 905, the storage device 919, or a removable recording medium 927. The ROM 903 stores programs, operation parameters, and the like used by the CPU 901. The RAM 905 temporarily stores programs used when the CPU 901 is executed, and parameters that change as appropriate when executing such programs. The CPU 901, the ROM 903, and the RAM 905 are connected to each other via the host bus 907 including an internal bus such as a CPU bus. In addition, the host bus 907 is connected to the external bus 911 such as a Peripheral Component Interconnect/Interface (PCI) bus via the bridge 909.

The input device 915 is a device operated by a user such as a mouse, a keyboard, a touchscreen, a button, a switch, and a lever. The input device 915 may include a microphone configured to detect voice of users. The input device 915 may be a remote control device that uses, for example, infrared radiation and another type of radio waves. Alternatively, the input device 915 may be external connection equipment 929 such as a mobile phone that corresponds to an operation of the information processing apparatus 10. The input device 915 includes an input control circuit that generates input signals on the basis of information which is input by a user to output the generated input signals to the CPU 901. A user inputs various types of data and indicates a processing operation to the information processing apparatus 10 by operating the input device 915. In addition, the imaging device 933 (to be described later) may function as the input device by capturing an image of movement of hands of a user or capturing a finger of a user. In this case, a pointing position may be decided in accordance with the movement of the hands or a direction of the finger.

The output device 917 includes a device that can visually or audibly report acquired information to a user. The output device 917 may be, for example, a display device such as a liquid crystal display (LCD), a plasma display panel (PDP), an organic electro-luminescence (EL) display, a projector, or a hologram display device, an audio output device such as a speaker or a headphone, or a printer. The output device 917 outputs a result obtained through a process performed by the information processing apparatus 10, in the form of text or video such as an image, or sounds such as voice and audio sounds. In addition, the output device 917 may include a light or the like to light the surroundings.

The storage device 919 is a device for data storage that is an example of the storage unit of the information processing apparatus 10. The storage device 919 includes, for example, a magnetic storage unit device such as a hard disk drive (HDD), a semiconductor storage device, an optical storage device, or a magneto-optical storage device. The storage unit 919 stores therein various data and programs executed by the CPU 901, and various data acquired from an outside.

The drive 921 is a reader/writer for the removable recording medium 927 such as a magnetic disk, an optical disc, a magneto-optical disk, and a semiconductor memory, and built in or externally attached to the information processing apparatus 10. The drive 921 reads out information recorded on the mounted removable recording medium 927, and outputs the information to the RAM 905. In addition, the drive 921 writes the record into the mounted removable recording medium 927.

The connection port 923 is a port used to directly connect equipment to the information processing apparatus 10. The connection port 923 may be a USB (Universal Serial Bus) port, an IEEE1394 port, and a Small Computer System Interface (SCSI) port, or the like. In addition, the connection port 923 may be an RS-232C port, an optical audio terminal, an HDMI (registered trademark) (High-Definition Multimedia Interface) port, and so on. The connection of the external connection equipment 929 to the connection port 923 makes it possible to exchange various kinds of data between the information processing apparatus 10 and the external connection equipment 929.

The communication device 925 is a communication interface including, for example, a communication device for connection to the communication network 931. The communication device 925 may be, for example, a wired or wireless local area network (LAN), Bluetooth (registered trademark), or a communication card for a wireless USB (WUSB). The communication device 925 may also be, for example, a router for optical communication, a router for asymmetric digital subscriber line (ADSL), or a modem for various types of communication. For example, the communication device 925 transmits and receives signals in the Internet or transmits signals to and receives signals from another communication device by using a predetermined protocol such as TCP/IP. The communication network 931 to which the communication device 925 connects is a network established through wired or wireless connection. The communication network 931 is, for example, the Internet, a home LAN, infrared communication, radio communication, or satellite communication.

The imaging device 933 is a device that captures images of a real space by using an image sensor such as a charge coupled device (CCD) or a complementary metal oxide semiconductor (CMOS), and various members such as a lens for controlling image formation of a subject image onto the image sensor, and generates the captured images. The imaging device 933 may capture a still image or a moving image.

The sensor 935 is various sensors such as an acceleration sensor, a gyro sensor, a geomagnetic sensor, an optical sensor, and a sound sensor. The sensor 935 acquires information regarding a state of the information processing apparatus 10 such as an attitude of a housing of the information processing apparatus 10, and information regarding an environment surrounding the information processing apparatus 10 such as luminous intensity and noise around the information processing apparatus 10. Moreover, the sensor 935 may include a global positioning system (GPS) sensor that receives GPS signals to measure latitude, longitude, and altitude of the device.

An example of the hardware configuration of the information processing apparatus 10 has been shown. Each of the above structural elements may include a general-purpose member, or may include hardware specialized for the function of each structural element. The configuration can be changed as appropriate, in accordance with the technology level at the time of performing the embodiment.

2. CONCLUSION

As described above, according to the embodiment of the present disclosure, there is provided an information processing apparatus including: a generation unit configured to generate second text data on the basis of first text data and information regarding a user's auditory characteristics; and an output unit configured to output output information regarding the second text data. The generation unit controls granularity of the second text data on the basis of the information regarding the user's auditory characteristics. This configuration can enhance the possibility of outputting information with granularity desired by the user.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

In addition, it is also possible to create a program for causing hardware such as a CPU, a ROM, and a RAM, which are embedded in a computer, to execute functions equivalent to the functions of the control unit 140. Moreover, it may be possible to provide a computer-readable recording medium having the program recorded thereon.

Note that the positions of the respective structural elements are not particularly limited as long as operation of the information processing system 1 is achieved. As a specific example, the image input unit 110, the operation input unit 115, the sound collection unit 120, the sensor unit 125, the communication unit 150, the storage unit 160, the audio output unit 170, and the display unit 180, and the control unit 140 may be provided in different apparatuses connected via a network. In this case, the control unit 140 may correspond to a server such as a web server or a cloud server, for example, and the image input unit 110, the operation input unit 115, the sound collection unit 120, the sensor unit 125, the communication unit 150, the storage unit 160, the audio output unit 170, and the display unit 180 may correspond to a client connected to the server via a network.

Moreover, not all the structural elements of the control unit 140 need to be accommodated in the same apparatus. For example, some of the acquisition unit 141, the generation unit 142, and the output unit 143 may be present in an apparatus that is different from the control unit 140. For example, the generation unit 141 may be present in a server that is different from the control unit 140 including the acquisition unit 141 and the output unit 143.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An information processing apparatus including:
a generation unit configured to generate second text data on a basis of first text data and information regarding a first user's auditory characteristics; and
an output unit configured to output output information regarding the second text data,
in which the generation unit controls granularity of the second text data on a basis of the information regarding the first user's auditory characteristics.

(2)
The information processing apparatus according to (1), in which the generation unit extracts, as one or more pieces of extracted data, one or more pieces of text data satisfying a predetermined relationship with a predetermined frequency region in which the first user's hearing level is low, from the first text data, and generates the second text data so as to include the one or more pieces of extracted data.

(3)
The information processing apparatus according to (2), in which the predetermined frequency region includes a range of frequencies in which the first user's hearing level is lower than a predetermined hearing level threshold.

(4)
The information processing apparatus according to any one of (1) to (3), in which the first text data includes text data based on content.

(5)
The information processing apparatus according to any one of (1) to (3), in which the first text data includes text data generated on a basis of speech of a second user.

(6)
The information processing apparatus according to (2) or (3), in which the generation unit divides the first text data into a plurality of pieces of divided data, calculates, for each of one or more pieces of divided data, a number of vowel elements of which at least one of corresponding one or more frequencies belongs to the frequency region, and extracts, as the one or more pieces of extracted data, one or more pieces of divided data for which the calculated number exceeds a predetermined number threshold, among the plurality of pieces of divided data.

(7)
The information processing apparatus according to any one of (1) to (6), including
an acquisition unit configured to acquire the information regarding the first user's auditory characteristics.

(8)
The information processing apparatus according to (7), in which the acquisition unit acquires the information regarding the first user's auditory characteristics on a basis of attribute information of the first user.

(9)
The information processing apparatus according to (7), in which the acquisition unit acquires the information regarding the first user's auditory characteristics, the information being registered in advance.

(10)
The information processing apparatus according to (7), in which the acquisition unit acquires the information regarding the first user's auditory characteristics on a basis of information regarding an environment where the first user is present.

(11)
The information processing apparatus according to (7), in which the acquisition unit acquires the information regarding the first user's auditory characteristics on a basis of activity information or biological information of the first user.

(12)
The information processing apparatus according to (3), including an acquisition unit configured to acquire the predetermined hearing level threshold.

(13)

The information processing apparatus according to (12), in which the generation unit updates the predetermined hearing level threshold on a basis of information regarding an environment where the first user is present.

(14)

The information processing apparatus according to (12), in which the generation unit updates the predetermined hearing level threshold on a basis of activity information or biological information of the first user.

(15)

The information processing apparatus according to any one of (1) to (14), in which the output unit outputs the output information again in a case where a predetermined condition is satisfied after the output information is output.

(16)

The information processing apparatus according to any one of (1) to (15), in which the output information includes at least one of sound information, image information, and vibration information generated on a basis of the second text data.

(17)

The information processing apparatus according to any one of (1) to (16), in which the generation unit makes the granularity of the second text data lower than granularity of the first text data.

(18)

The information processing apparatus according to (17), in which the generation unit makes the granularity of the second text data lower than the granularity of the first text data by excluding a predetermined word from the first text data.

(19)

An information processing method including:
generating second text data on a basis of first text data and information regarding a first user's auditory characteristics;
outputting output information regarding the second text data; and
controlling, by a processor, granularity of the second text data on a basis of the information regarding the first user's auditory characteristics.

(20)

A program for causing a computer to function as an information processing apparatus including:
a generation unit configured to generate second text data on a basis of first text data and information regarding a first user's auditory characteristics; and
an output unit configured to output output information regarding the second text data,
in which the generation unit controls granularity of the second text data on a basis of the information regarding the first user's auditory characteristics.

REFERENCE SIGNS LIST

1 information processing system
10 information processing apparatus
110 image input unit
115 operation input unit
120 sound collection unit
125 sensor unit
140 control unit
141 acquisition unit
142 generation unit
143 output unit
150 communication unit
160 storage unit
170 audio output unit
180 display unit

The invention claimed is:

1. An information processing apparatus comprising:
a generation unit configured to generate second text data on a basis of first text data and information regarding a first user's auditory characteristics; and
an output unit configured to output output information regarding the second text data,
wherein the generation unit controls granularity of the second text data on a basis of the information regarding the first user's auditory characteristics,
wherein the information regarding the first user's auditory characteristics includes a hearing level that indicates capability of catching sound information,
wherein the generation unit extracts, as one or more pieces of extracted data, one or more pieces of text data from the first text data, and generates the second text data so as to include the one or more pieces of extracted data, and
wherein the generation unit and the output unit are each implemented via at least one processor.

2. The information processing apparatus according to claim 1, wherein the generation unit extracts, from the first text data and as the one or more pieces of extracted data, one or more pieces of text data satisfying a predetermined relationship with a predetermined frequency region in which the first user's hearing level is low.

3. The information processing apparatus according to claim 2, wherein the predetermined frequency region includes a range of frequencies in which the first user's hearing level is lower than a predetermined hearing level threshold.

4. The information processing apparatus according to claim 1, wherein the first text data includes text data based on content.

5. The information processing apparatus according to claim 1, wherein the first text data includes text data generated on a basis of speech of a second user.

6. The information processing apparatus according to claim 2, wherein the generation unit divides the first text data into a plurality of pieces of divided data, calculates, for each of one or more pieces of divided data, a number of vowel elements of which at least one of corresponding one or more frequencies belongs to the frequency region, and extracts, as the one or more pieces of extracted data, one or more pieces of divided data for which the calculated number exceeds a predetermined number threshold, among the plurality of pieces of divided data.

7. The information processing apparatus according to claim 1, comprising
an acquisition unit configured to acquire the information regarding the first user's auditory characteristics,
wherein the acquisition unit is implemented via at least one processor.

8. The information processing apparatus according to claim 7, wherein the acquisition unit acquires the information regarding the first user's auditory characteristics on a basis of attribute information of the first user.

9. The information processing apparatus according to claim 7, wherein the acquisition unit acquires the information regarding the first user's auditory characteristics, the information being registered in advance.

10. The information processing apparatus according to claim 7, wherein the acquisition unit acquires the information regarding the first user's auditory characteristics on a basis of information regarding an environment where the first user is present.

11. The information processing apparatus according to claim 7, wherein the acquisition unit acquires the information regarding the first user's auditory characteristics on a basis of activity information or biological information of the first user.

12. The information processing apparatus according to claim 3, comprising
an acquisition unit configured to acquire the predetermined hearing level threshold,
wherein the acquisition unit is implemented via at least one processor.

13. The information processing apparatus according to claim 12, wherein the generation unit updates the predetermined hearing level threshold on a basis of information regarding an environment where the first user is present.

14. The information processing apparatus according to claim 12, wherein the generation unit updates the predetermined hearing level threshold on a basis of activity information or biological information of the first user.

15. The information processing apparatus according to claim 1, wherein the output unit outputs the output information again in a case where a predetermined condition is satisfied after the output information is output.

16. The information processing apparatus according to claim 1, wherein the output information includes at least one of sound information, image information, and vibration information generated on a basis of the second text data.

17. The information processing apparatus according to claim 1, wherein the generation unit makes the granularity of the second text data lower than granularity of the first text data.

18. The information processing apparatus according to claim 17, wherein the generation unit makes the granularity of the second text data lower than the granularity of the first text data by excluding a predetermined word from the first text data.

19. An information processing method comprising:
generating second text data on a basis of first text data and information regarding a first user's auditory characteristics;
outputting output information regarding the second text data; and
controlling, by a processor, granularity of the second text data on a basis of the information regarding the first user's auditory characteristics,
wherein the information regarding the first user's auditory characteristics includes a hearing level that indicates capability of catching sound information, and
wherein one or more pieces of extracted data are obtained from extracting one or more pieces of text data from the first text data, and the second text data is generated so as to include the one or more pieces of extracted data.

20. A non-transitory computer-readable medium having embodied thereon a program, which when executed by a computer causes the computer to execute a method, the method comprising:
generating second text data on a basis of first text data and information regarding a first user's auditory characteristics;
outputting output information regarding the second text data; and
controlling granularity of the second text data on a basis of the information regarding the first user's auditory characteristics,
wherein the information regarding the first user's auditory characteristics includes a hearing level that indicates capability of catching sound information, and
wherein one or more pieces of extracted data are obtained from extracting one or more pieces of text data from the first text data, and the second text data is generated so as to include the one or more pieces of extracted data.

* * * * *